(12) United States Patent
Mjalli et al.

(10) Patent No.: US 7,501,538 B2
(45) Date of Patent: Mar. 10, 2009

(54) ARYL AND HETEROARYL COMPOUNDS, COMPOSITIONS AND METHODS OF USE

(75) Inventors: Adnan M. M. Mjalli, Oak Ridge, NC (US); Guoxiang Huang, Greensboro, NC (US); Murty N. Arimilli, Oak Ridge, NC (US); Thomas Scott Yokum, Greensboro, NC (US); Jeff Jiqun Zhu, Greensboro, NC (US); Muralidhar Bondlela, Greensboro, NC (US)

(73) Assignee: TransTech Pharma, Inc., High Point, NC (US)

( * ) Notice: Subject to any disclaimer, the term of this patent is extended or adjusted under 35 U.S.C. 154(b) by 202 days.

(21) Appl. No.: 10/913,882

(22) Filed: Aug. 6, 2004

(65) Prior Publication Data

US 2005/0049310 A1 Mar. 3, 2005

Related U.S. Application Data

(60) Provisional application No. 60/493,903, filed on Aug. 8, 2003, provisional application No. 60/493,879, filed on Aug. 8, 2003, provisional application No. 60/493,878, filed on Aug. 8, 2003.

(51) Int. Cl.
C07C 229/00 (2006.01)

(52) U.S. Cl. .................. 562/450; 562/442; 562/443; 562/433

(58) Field of Classification Search ................. 562/429, 562/405, 433, 450, 456, 445; 560/19, 34, 560/35, 59, 83; 564/80, 84, 155
See application file for complete search history.

(56) References Cited

U.S. PATENT DOCUMENTS

| | | | |
|---|---|---|---|
| 4,717,736 A | 1/1988 | Rokach et al. | |
| 5,518,735 A | 5/1996 | Sturzebecher et al. | |
| 5,679,671 A | 10/1997 | Oinuma et al. | |
| 5,750,520 A | 5/1998 | Danilewicz et al. | |
| 5,780,498 A | 7/1998 | Frueh et al. | |
| 5,977,075 A | 11/1999 | Ksander et al. | |
| 6,001,820 A | 12/1999 | Hirsh et al. | |
| 6,087,380 A | 7/2000 | Hauel et al. | |
| 6,093,731 A | 7/2000 | Dickinson et al. | |
| 6,194,448 B1 | 2/2001 | Bredrget et al. | |
| 6,194,458 B1 | 2/2001 | Baker et al. | |
| 6,262,084 B1 | 7/2001 | Biediger et al. | |
| 6,284,871 B1 | 9/2001 | Mertens et al. | |
| 6,291,511 B1 | 9/2001 | Durette et al. | |
| 6,342,504 B1 | 1/2002 | Brunk et al. | |
| 6,358,978 B1 | 3/2002 | Ritzeler et al. | |
| 6,528,655 B1 | 3/2003 | N'Zemba et al. | |
| 6,559,174 B2 | 5/2003 | Lin et al. | |
| 6,743,790 B2 | 6/2004 | Klingler et al. | |
| 6,855,843 B2 * | 2/2005 | Sircar et al. ............ 560/38 |
| 6,908,939 B2 | 6/2005 | Bernadon et al. | |
| 7,122,580 B2 | 10/2006 | Mjalli et al. | |
| 2002/0016461 A1 | 2/2002 | Albers et al. | |
| 2002/0095041 A1 | 7/2002 | Chan et al. | |
| 2002/0103192 A1 | 8/2002 | Curtin et al. | |
| 2002/0151595 A1 | 10/2002 | Ries et al. | |
| 2002/0173656 A1 | 11/2002 | Peyman et al. | |
| 2002/0198195 A1 | 12/2002 | Nazare et al. | |
| 2003/0149083 A1 | 8/2003 | Tanaka et al. | |
| 2004/0106626 A1 | 6/2004 | South et al. | |
| 2004/0126856 A1 | 7/2004 | Bajaj et al. | |
| 2005/0065346 A1 | 3/2005 | Ries et al. | |
| 2005/0256116 A1 | 11/2005 | Clary et al. | |

FOREIGN PATENT DOCUMENTS

| | | |
|---|---|---|
| DE | 199 28 424 | 12/2000 |
| EP | 0150118 | 9/1987 |
| EP | 1213288 | 12/2002 |
| FR | 2 847 251 | 5/2004 |
| GB | 1 501 541 | 2/1978 |
| GB | 2354440 | 7/2000 |
| JP | 2001-089368 | 4/2001 |
| WO | WO 95/12611 | 11/1995 |
| WO | WO 98/37075 | 8/1998 |
| WO | WO 98/53817 | 12/1998 |
| WO | WO 99/26923 | 6/1999 |
| WO | WO 99/36393 | 7/1999 |

(Continued)

OTHER PUBLICATIONS

Sircar, CAS online citation 131:116517 [retrieved May 29, 2008] from STN; Columbus, OH, USA.*

(Continued)

*Primary Examiner*—Karl J Puttlitz
(74) *Attorney, Agent, or Firm*—Kilpatrick Stockton LLP

(57) ABSTRACT

This invention provides aryl and heteroaryl compounds of Formula (I) as described herein, and methods of their preparation. Also provided are pharmaceutical compositions made with the compounds of Formula (I) and methods for making such compositions. The compounds of Formula (I) may activate an erythropoietin receptor and thus, may be useful to induce red blood cell production. The compounds of Formula (I) and compositions including compounds of Formula (I) may be useful in a variety of applications including the management, treatment and/or control of diseases caused at least in part by deficient (or inefficient) EPO production relative to hemoglobin level.

28 Claims, No Drawings

FOREIGN PATENT DOCUMENTS

| WO | WO 00/35864 | 6/2000 |
| --- | --- | --- |
| WO | WO 00-35864 | 6/2000 |
| WO | WO 00/37429 | 6/2000 |
| WO | WO 00/67746 | 11/2000 |
| WO | WO 00/68188 | 11/2000 |
| WO | WO 00/76971 | 12/2000 |
| WO | WO 01/10823 | 2/2001 |
| WO | WO 01/21584 | 3/2001 |
| WO | WO 01/38309 | 5/2001 |
| WO | WO 01/68586 | 9/2001 |
| WO | WO 02/18320 | 3/2002 |
| WO | WO 02/26717 | 4/2002 |
| WO | WO 02/062748 | 8/2002 |
| WO | WO 02/085841 | 10/2002 |
| WO | WO 03/007945 | 1/2003 |
| WO | WO 03/033496 | 4/2003 |
| WO | WO 2004/014844 | 2/2004 |
| WO | WO 2004/046091 | 6/2004 |
| WO | WO 2004/080970 | 9/2004 |
| WO | WP 2004/084842 | 10/2004 |

OTHER PUBLICATIONS

Chen et al., Anti-Cancer Drug Design (1996), 11(1), 49-71; CAS online citation 124:306500 [retrieved May 29, 2008] from STN; Columbus, OH, USA.*

Bebernitz et al., "Anilides of R-Trifluoro-2-hydroxy-2-methylpropionic Acid as Inhibitors of Pyruvate Dehydrogenase Kinase", Journal of Medicinal Chemistry, vol. 43, pp. 7121-7124, (2000).

Shrader et al., "Neutral Inhibitors of the Serine Protease Factor Xa", Bioorganic & Medicinal Chemistry Letters, vol. 11, pp. 1801-1804, (2001).

Knowles et al., "Photochemical alkylation of glycine leading to phenylalanines", Tetrahedron Letters, vol. 41, pp. 7121-7124, (2000).

Burdick et al, "N-Benzoyl Amino Acids as LFA-1/ICAM Inhibitors 1: Amino Acid Structure-Activity Relationship" Bioorganic Medicinal Chemistry Letters, vol. 13, pp. 1015-1018 (2003).

Castanedo et al, "Solid-Phase synthesis of dual alpha4beta1/alpha4beta7 Integrin antagonists: Two Scaffolds with Overlapping Pharmacophores", Bioorganic & Medicinal Chemistry Letters, Oxford, GB vol. 12, pp. 2913-2917 (2002).

Database Caplus Chemical Abstracts Service, Columbus, Ohio, US, XP002319820, rerieed from STN Database accession No. 1973:504834 abstract; RN 42787-97-3 abstract & I. Hahnemann et al. Journal Fuer Praktische Chemie, vol. 315, No. 4, 1973, pp. 796-800.

Greenspan P.D. et al., "N-aryl Cinnamides: A Novel Class of Rigid and Highly Potent Leukotriene B4 Receptor Antagonists", Bioorganic and Medicinal Chemistry Letters, vol. 7, pp. 949-954 (1997).

International Search Report for related PCT application PCT/US2004/025463 mailed Jan. 26, 2005.

International Search Report for related PCT application PCT/US2004/025478 mailed Jan. 26, 2005.

International Search Report for related PCT application PCT/US2004/025429 mailed Jan. 26, 2005.

International Search Report for PCT application PCT/US03/25045 mailed Mar. 14, 2005.

Knowles, H.S. et al., "A photochemical approach to phenylalanines and related compounds by alkylation of glycine", Tetrahedron, vol. 57, pp. 98115-98124 (2001).

O'Donnell M.J. et al., "Enantioselective Solid-Phase Synthesis of α-Amino Acid Derivatives", Tetrahedron, vol. 55, pp. 6347-6362 (1999).

Sircar et al, "Synthesis and SAR of N-benzoyl-L-Biphenylalanine derivatives: Discovery of TR-14035, A Dual Alpha4Beta7/Alpha4Beta1 Intergrin Antagonist", Bioorganic & Medicinal Chemistry, vol. 10, pp. 2051-2066 (2002).

Office Action mailed Jul. 9, 2007 for U.S. Appl. No. 10/913,168.

Office Action mailed Mar. 20, 2007 for U.S. Appl. No. 10/913,168.

Amendment mailed to USPTO on Apr. 16, 2007 for U.S. Appl. No. 10/913,168.

Office Action mailed Jun. 22, 2007 for U.S. Appl. No. 10/913,216.

Office Action mailed Feb. 1, 2007 for U.S. Appl. No. 10/913,216.

Office Action mailed Sep. 26, 2006 for U.S. Appl. No. 10/913,216.

Response Under 37 C F R § 1 111 mailed to USPTO on May 1, 2007 for U.S. Appl. No. 10/913,218.

Amendment and Response mailed to USPTO on Nov. 27, 2006 for U.S. Appl. No. 10/913,216.

Preliminary Amendment mailed to USPTO on Nov. 12, 2004 for U.S. Appl. No. 10/913,216.

Interview Summary mailed Feb. 1, 2007 for U.S. Appl. No. 10/913,216.

Patent Cooperation Treaty Notification Concerning Transmittal of International Preliminary Report on Patentability and Written Opinion of the International Searching Authority for Application Serial No. PCT/US2004/025463 dated Jan. 24, 2005.

Patent Cooperation Treaty Notification Concerning Transmittal of International Preliminary Report on Patentability and Written Opinion of the International Searching Authority for Application Serial No. PCT/US2004/025429 dated Jan. 24, 2005.

Patent Cooperation Treaty Notification Concerning Transmittal of International Preliminary Report on Patentability and Written Opinion of the International Searching Authority for Application Serial No. PCT/US2004/025478 dated Jan. 24, 2005.

Bernardon et al CAS 139 101121.

Srivastava et al. 1981, CAS 95 125911.

ST Hilaire et al CAS 141 150947.

* cited by examiner

ARYL AND HETEROARYL COMPOUNDS, COMPOSITIONS AND METHODS OF USE

STATEMENT OF RELATED APPLICATIONS

The present application claims priority under 35 USC 119 from the following U.S. Provisional Patent Applications: Ser. No. 60/493,879, filed Aug. 8, 2003, entitled "Aryl and Heteroaryl Compounds as Antviral Agents"; Ser. No. 60/493,878, filed Aug. 8, 2003, entitled "Aryl and Heteroaryl Compounds and Methods to Modulate Red Blood Cell Production"; Ser. No. 60/493,903, filed Aug. 8, 2003, entitled "Aryl and Heteroaryl Compounds and Methods to Modulate Coagulation", the entirety of which are herein incorporated by reference.

FIELD OF THE INVENTION

This invention relates to aryl and heteroaryl compounds and compositions that may bind to and activate erythropoietin receptors, and methods of use of such compounds and compositions.

BACKGROUND OF THE INVENTION

Erythropoietin (EPO) is a 165 amino acid, 34 kilodalton (kDa) glycoprotein hormone which is the principal factor responsible for the regulation of red blood cell production during steady-state conditions and for accelerating recovery of red blood cell mass following hemorrhage. The primary site for EPO synthesis in adult organisms is the kidney. The liver synthesizes lower levels of EPO, and some evidence suggests that there is an additional contribution from macrophages in the bone marrow. The primary stimulus for increased EPO synthesis is tissue hypoxia, which results from decreased blood $O_2$ availability [Jelkmann, W., Physiol. Reviews, 72: 449 (1992)]. The principal function of EPO is to act in concert with other growth factors to stimulate the proliferation and maturation of responsive bone marrow erythroid precursor cells.

A gene for a human EPO receptor (EPO-R) has been isolated and mapped to the p region of chromosome 19 [Winkelman, J. C. et al., Blood, 76: 24 (1990)]. cDNA analysis predicts this receptor to be a 55 kDa, 508 amino acid residue transmembrane protein comprised of a 24 amino acid signal peptide, a 226 amino acid external segment, a 22 amino acid transmembrane segment, and a 236 amino acid cytoplasmic domain [Youssoufian, H. et al., Blood, 81: 2223 (1993)]. The properties of this receptor, including the presence of a set of four conserved cysteine residues and a WSXWS motif in the external segment, place it in the hematopoietin/cytokine superfamily of receptors that also includes the receptors for interelukins IL-3, IL-4, IL-6, IL-7, granulocyte colony-stimulating factor (G-CSF), granulocyte macrophage colony-stimulating factor (GM-CSF), the beta-subunit of the IL-2 receptor and others [Cosman, D., Cytokine 5:95 (1993)]. Cells known to express EPO-R include megakaryocytes, erythoid progenitors, endothelial cells, and, possibly, neurons [Landschulz, K. T. et al., Blood 73: 1476 (1989); Youssoufian, H. et al., Blood 81: 2223 (1993); Fraser, J. K. et al., Exp. Hematol., 17: 10 (1989); Anagnostou, A. et al., Proc. Natl. Acad. Sci. USA, 91: 3974 (1994); and Digicaylioglu, M. et al., Proc. Natl. Acad. Sci. USA, 92: 3717 (1995)].

Ligand binding studies demonstrate the existence of distinct high (Kd=75-100 pM) and low (Kd=220-800 pM) affinity receptors for EPO [Broudy, V. C. et al., Blood, 77: 2583 (1991); Harris, K. W. et al., J. Biol. Chem., 267: 15205 (1992); and Landschulz, K. T. et al., Blood, 73: 1476 (1989)], and cross-linking studies show the presence of multiple cross-linked species [Miura, O. and J. Ihle, Blood, 81: 1739 (1993)]. EPO-R dimerization and janus kinase 2 (JAK2) activation are considered to be first steps in the signal transduction process [Watowich, S. S. et al., Proc. Natl. Acad. Sci. USA, 89: 2140 (1992); Witthuhn, B. A. et al., Cell, 74: 227 (1993); and Tanner, J. W. et al., J. Biol. Chem., 270: 6523 (1995)].

Although the details of the interactions of the components of the EPO receptor complex and the mechanism of signal transduction by this complex are not yet fully understood, x-ray crystallography studies suggest that the EPO-R when not bound to a ligand (i.e., "unliganded") exists as a dimer in an open-scissors-like conformation with the C-terminal end of the subdomain 2 regions being over 70 angstroms apart [Livnah, O. et al., Science, 283: 987 (1999)]. In the ligand bound EPO-R/EPO structure (i.e., "liganded EPO-R/EPO"), these C-terminal regions become much closer (~30 angstroms). Thus, it is envisioned that the preformed EPO-R dimer, by keeping the cytoplasmic domains apart, is in an inactivated state, but ligand occupancy brings the extracellular and cytoplasmic domains into proximity to allow signaling. Fragment complementation assays confirmed these data by demonstrating a dramatic ligand-induced enhancement of proximity of the cytoplasmic domain of EPO-R dimers [Remy, I. et al., Science, 283: 990 (1999)]. Together, these studies implicate the existence of preformed EPO-R dimers that are activated by a distinct conformational change in response to ligand.

Within the erythroid lineage, EPO seems to act in concert with other growth factors such as stem cell factor (SCF), insulin-like growth factor-I (IGF-I), and interleukin-3 (IL-3) to ensure the expansion and maturation of immature erythrocytes [Muta, K. et al., J. Clin. Invest., 94: 34 (1994)]. In particular, EPO has been found to interrupt the normal apoptotic cycle experienced by erythroid progenitors as they progress from erythrocyte colony forming units (CFU-E) through the basophilic erythroblast stage [Koury, M. J. and M. C. Bondurant, Science, 248: 378 (1990); and Nijhof, W. et al., Exp. Hematol., 23: 369 (1995)].

In conjunction with IL-3, EPO also seems to have an effect on the earliest erythroid precursor, the erythrocyte burst forming unit (BFU-E), which gives rise to CFU-E. In this case, evidence suggests its activities are not limited to maintaining cell viability. Both IL-3 and EPO are reported to induce proliferation of BFU-E, but only EPO seems capable of initiating differentiation/maturation of BFU-E [Carroll, M. et al., Proc. Natl. Acad. Sci. USA, 92: 2869 (1995); Liboi, E. et al., Proc. Natl. Acad. Sci. USA, 90: 11351 (1993); Krosl, J. et al., Blood, 85: 50 (1995); and Dai, C. H. et al., Blood, 78: 2493 (1991)].

Deficient (or inefficient) EPO production relative to hemoglobin level is associated with certain forms of anemia. These include anemia of renal failure and end-stage renal disease [Kurtz, A. and Eckardt, K-U., Contrib. Nephrol., 87: 15 (1990)], anemia of chronic disorders (chronic infections and rheumatoid arthritis) [Means, R. T., Stem Cells, 13: 32 (1995)], autoimmune diseases [Jelkmann, W., Physiol. Reviews, 72: 449 (1992)], AIDS [Doweiko, J. P., Blood Reviews, 7:121 (1993)], and malignancy [Miller, C. B. et al., New Engl. J. Med., 322: 1689 (1990)]. Many of these conditions are associated with the generation of inerleukin-1 (IL-1) and a factor that has been shown to be an inhibitor of EPO activity [Jelkman, W. E. et al., Ann. NY Acad. Sci., 718: 300 (1994); and Jelkman, W. et al., Life Sci., 50: 301 (1991)].

At present, the primary treatment for anemia induced by these conditions is the administration of recombinant EPO via subcutaneous or intravenous injection. While the use of recombinant EPO has significantly improved the quality of life of these patients, there are some hardships associated with EPO treatment in that chronic treatment requires repeated administration by injection, which is both inconvenient and costly for the patient. Thus, the discovery of effective and safe orally active small molecular EPO mimetics has the potential to enhance the standard of therapy beyond the current recombinant EPO therapy.

SUMMARY OF THE INVENTION

Embodiments of the present invention provide aryl and heteroaryl compounds, compositions, and methods of use of such compounds and compositions. The present invention may be embodied in a variety of ways.

In one embodiment, the present invention comprises compounds of Formula (I) as described herein. In another embodiment, the present invention also provides methods for the preparation of compounds of Formula (I).

The present invention also comprises pharmaceutical compositions comprising compounds of Formula (I). In another embodiment, the present invention provides methods for the preparation of compositions comprising the compounds of Formula (I). The pharmaceutical compositions may comprise pharmaceutically acceptable carriers, excipients, and/or diluents.

In another embodiment, the present invention provides methods for the use of compounds of Formula (I) and pharmaceutical compositions comprising compounds of Formula (I). In one embodiment, the compounds and pharmaceutical compositions of the present invention may be used for treating human or animal disorders. For example, the compounds and pharmaceutical compositions of the present invention may be used for the treatment, management, and/or control of diseases mediated at least in part by the erythropoietin (EPO) receptor. Such diseases or disease states may include anemia of renal failure and end-stage renal disease, anemia of chronic disorders (chronic infections and rheumatoid arthritis), autoimmune diseases, AIDS, and malignancy.

The compounds and pharmaceutical compositions of the present invention may provide a number of advantages when used for treating human or animal disorders. Induction of red blood cell production with agents that selectively bind to, and activate, an erythropoietin receptor may alleviate the hypoxia-related conditions associated with certain forms of anemia. In certain embodiments of the present invention, compounds of Formula (I) may induce red blood cell production by binding to and activating an erythropoietin receptor. Compounds of Formula (I) may therefore be particularly advantageous when used for the management, treatment, and control of diseases in humans caused in part by deficient (or inefficient) EPO production (i.e., relative to hemoblobin levels) associated with certain forms of anemia.

Additionally, compounds and pharmaceutical compositions of the present invention may provide a variety of treatment options. The compounds and pharmaceutical compositions of the present invention may be administered by routes other than injection, which can be the preferred route of administration for recombinant EPO. As small molecule EPO mimetics, example embodiments of the compounds and pharmaceutical compositions of the present invention may be administered orally, topically, or parentally. Also, the compounds and pharmaceutical compositions of the present invention may comprise a primary therapeutic or may be used as an adjunct to other therapeutics.

Additional features of the present invention will be described hereinafter. It is to be understood that the invention is not limited in its application to the details set forth in the foregoing or following description but is capable of other embodiments and of being practiced or carried out in various ways.

DETAILED DESCRIPTION

Embodiments of the present invention provide compounds, compositions and methods of use for such compounds. In certain embodiments, the compounds and compositions of the present invention may bind to, and activate, an erythropoietin receptor.

Embodiments of the present invention comprise compounds of Formula (I) as depicted below. Embodiments of the present invention also comprise methods of the preparation of compounds of Formula (I) and/or pharmaceutical compositions comprising compounds of Formula (I). In certain embodiments, compounds of Formula (I) may useful inducers of red blood cell production by binding to and activating an erythropoietin receptor.

In other embodiments, the present invention provides methods for the use of compounds of Formula (I) and pharmaceutical compositions comprising compounds of Formula (I) in treating human or animal disorders. Compounds of Formula (I) and pharmaceutical compositions comprising compounds of Formula (I) may be useful in a variety of applications. Certain embodiments of the compounds and/or compositions of the present invention may be used for the management, treatment, and/or control, of diseases in humans. Such diseases may be caused in part by deficient (or inefficient) EPO production (measured relative to hemoglobin level). For example, deficiencies of EPO may result in anemia of renal failure and end-stage renal disease, anemia of chronic disorders (chronic infections and rheumatoid arthritis), autoimmune diseases, AIDS, and malignancy.

In one aspect, the present invention provides a compound comprising at least one moiety of the Formula (I):

(I)

wherein c is equal to 0, 1, or 2; wherein the values of 0, 1, and 2 comprise a direct bond, —$CH_2$—, and —$CH_2$—$CH_2$—, optionally substituted 1 to 4 times with a substituent group, wherein said substituent group(s) or the term substituted refers to groups comprising: -alkyl, -aryl, -alkylene-aryl, -arylene-alkyl, -alkylene-arylene-alkyl, —O-alkyl, —O-aryl, or -hydroxyl. In one embodiment, c is equal to 0 or 1. In another embodiment, c is equal to 0.

G comprises -hydrogen, —$CO_2R_1$, —$CH_2OR_1$, —C(O)—$R_1$, —$C(R_1)$=N—O—$R_2$, or an acid isostere, wherein $R_1$ and $R_2$ independently comprise -hydrogen, -alkyl, -aryl, -arylene-alkyl, -alkylene-aryl, or -alkylene-arylene-alkyl. In one embodiment, G may comprise -hydrogen or —$CO_2R_1$, wherein $R_1$ comprises -hydrogen, -alkyl, or -aryl. In another embodiment, G may comprise -hydrogen or —$CO_2H$.

V comprises —$(CH_2)_b$—O—$(CH_2)_a$—, —$(CH_2)_b$—N($R_7$)—$(CH_2)_a$—, —$(CH_2)_b$—O—, —$(CH_2)_b$—N($R_7$), —$(CH_2)_a$—, or a direct bond, in which a is equal to 0, 1, or 2, b is equal to 1 or 2, and $R_7$ comprises -hydrogen, -alkyl, -aryl, -arylene-alkyl, -alkylene-aryl, or -alkylene-arylene-alkyl; wherein the —$(CH_2)$— group(s) may be optionally substituted 1 to 4 times with a substituent group comprising -alkyl, -aryl, -alkylene-aryl, -arylene-alkyl, -alkylene-arylene-alkyl, —O-alkyl, —O-aryl, or -hydroxyl. In an embodiment, V comprises —$(CH_2)_a$—, —$(CH_2)_b$—O—$(CH_2)_a$—, or a direct bond, wherein a is equal to 1 or 2, and b is equal to 1. In another embodiment, V comprises —$(CH_2)_a$— or a direct bond, wherein a is equal to 1.

X comprises —$N(R_8)$—, —$CON(R_8)$—, —$N(R_8)CO$—, —$N(R_8)CON(R_9)$—, —$OC(O)N(R_8)$—, —$N(R_8)C(O)O$—, —$SO_2N(R_8)$—, —$N(R_8)SO_2$—, or —$N(R_8)SO_2N(R_9)$—, wherein $R_8$ and $R_9$ independently comprise -hydrogen, -alkyl, -aryl, -arylene-alkyl, -alkylene-aryl, or -alkylene-arylene-alkyl. In another embodiment, X comprises —$N(R_8)$—, —$CON(R_8)$—, —$N(R_8)CO$—, —$SO_2N(R_8)$—, or —$N(R_8)SO_2$—, wherein $R_8$ may independently comprise—hydrogen, -alkyl, -aryl, -arylene-alkyl, -alkylene-aryl, or -alkylene-arylene-alkyl. In yet another embodiment, X may comprise —$N(R_8)$—, —$N(R_8)CO$—, or —$CON(R_8)$—, wherein $R_8$ may comprise -hydrogen, -alkyl, -aryl, -arylene-alkyl, -alkylene-aryl, or -alkylene-arylene-alkyl.

$Ar_1$ comprises an aryl, heteroaryl, fused cycloalkylaryl, fused cycloalkylheteroaryl, fused heterocyclylaryl, or fused heterocyclylheteroaryl group optionally substituted 1 to 7 times. In one embodiment, $Ar_1$ comprises a mono- or bicyclic aryl or heteroaryl group optionally substituted 1 to 7 times. In another embodiment, $Ar_1$ comprises a phenyl group having 1 to 5 substituents. The substituents for the various embodiments of $Ar_1$ may independently comprise:

a) -fluoro;
b) -chloro;
c) -bromo;
d) -iodo;
e) -cyano;
f) -nitro;
g) -perfluoroalkyl;
h) -D-$R_{10}$;
i) -alkyl;
j) -aryl;
k) -heteroaryl;
l) -heterocyclyl;
m) -cycloalkyl;
n) -alkylene-aryl;
o) -alkylene-arylene-aryl;
p) -alkylene-arylene-alkyl;
q) -arylene-alkyl;
r) -arylene-arylene-alkyl;
s) -D-alkyl;
t) -D-aryl;
u) -D-alkylene-aryl;
v) -D-arylene-alkyl;
w) -D-alkylene-arylene-aryl;
x) -D-arylene-arylene-aryl;
y) -D-alkylene-arylene-alkyl;
z) -alkylene-D-alkylene-aryl;
aa) -arylene-D-alkyl;
bb) -alkylene-D-aryl;
cc) -alkylene-D-heteroaryl;
dd) -alkylene-D-cycloalkyl;
ee) -alkylene-D-heterocyclyl;
ff) -alkylene-D-arylene-alkyl;
gg) -alkylene-D-alkylene-arylene-alkyl;
hh) -alkylene-D-alkyl;
ii) -alkylene-D-$R_{10}$;
jj) -arylene-D-$R_{10}$; or
kk) -hydrogen;

wherein D comprises —$CH_2$—, —O—, —$N(R_{11})$—, —$C(O)$—, —$CON(R_{11})$—, —$N(R_{11})C(O)$—, —$N(R_{11})CON(R_{12})$—, —$N(R_{11})C(O)O$—, —$OC(O)N(R_{11})$—, —$N(R_{11})SO_2$—, —$SO_2N(R_{11})$—, —$C(O)$—O—, —O—$C(O)$—, —S—, —$S(O)$—, —$S(O_2)$—, —$N(R_{11})SO_2N(R_{12})$—,

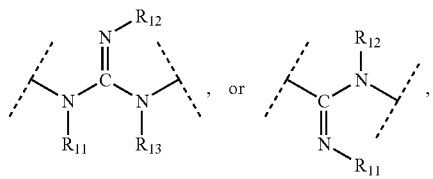

and wherein $R_{10}$, $R_{11}$, $R_{12}$, and $R_{13}$ independently comprise -hydrogen, -alkyl, -aryl, -arylene-alkyl, -alkylene-aryl, or -alkylene-arylene-alkyl. In another embodiment, $Ar_1$ may comprise a mono-substituted phenyl group wherein the substituent comprises -aryl, -arylene-alkyl, -D-aryl, -D-alkylene-arylene-alkyl, -arylene-D-alkyl, -arylene-D-$R_{10}$, or -D-alkylene-arylene-aryl, wherein $R_{10}$ compromises -aryl, or -alkylene-aryl, and D comprises —O—, —$N(R_{11})$—, —$CON(R_{11})$—, or —$N(R_{11})C(O)$—, wherein $R_{11}$ comprises -hydrogen, -alkyl, or -aryl. In yet another embodiment, $Ar_1$ may comprise biphenyl-4-yl, trifluoromethyl-biphenyl-4-yl, (biphenyl-4-ylmethoxy)-phenyl, (tert-butyl-benzyloxy)-phenyl, or 4'-phenoxy-biphenyl4-yl.

$Ar_2$ comprises an aryl or heteroaryl group optionally substituted 1 to 7 times. In one embodiment, $Ar_2$ may comprise a phenyl, naphthyl, pyridyl, isoquinolyl, pyrimidyl or quinazolyl group optionally substituted 1 to 7 times. In another embodiment, $Ar_2$ may comprise a substituted phenyl, 2-naphthyl, 2-pyridyl, 3-isoquinolyl, 2-pyrimidyl or 2-quinazolyl group having 1 to 5 substituents. The substituents for the various embodiments of $Ar_2$ may independently comprise:

a) -fluoro;
b) -chloro;
c) -bromo;
d) -iodo;
e) -cyano;
f) -nitro;
g) -perfluoroalkyl;
h) -$T_1$-$R_{14}$;
i) -alkyl;
i) -aryl;
k) -heteroaryl;
l) -heterocyclyl;
m) -cycloalkyl;
n) -alkylene-aryl;
o) -alkylene-arylene-aryl;
p) -alkylene-arylene-alkyl;
q) -arylene-alkyl;
r) -arylene-arylene-alkyl;
s) -$T_1$-alkyl;
t) -$T_1$-aryl;
u) -$T_1$-alkylene-aryl;
v) -$T_1$-arylene-aryl;
w) -$T_1$-arylene-alkyl;
x) -$T_1$-alkylene-arylene-aryl;
y) -$T_1$-arylene-arylene-aryl;
z) -$T_1$-alkylene-arylene-alkyl;

aa) -T$_1$-alkylene-T$_2$-R$_{14}$;
bb) -T$_1$-arylene-T$_2$-R$_{14}$
cc) -alkylene-T$_1$-alkylene-aryl;
dd) -arylene-T$_1$-alkyl;
ee) -alkylene-T$_1$-aryl;
ff) -alkylene-T$_1$-heteroaryl;
gg) -alkylene-T$_1$-cycloalkyl;
hh) -alkylene-T$_1$-heterocyclyl;
ii) -alkylene-T$_1$-arylene-alkyl;
jj) -alkylene-T$_1$-alkylene-arylene-alkyl;
kk) -alkylene-T$_1$-alkyl;
ll) -alkylene-T$_1$-R$_{14}$;
mm) -arylene-T$_1$-R$_{14}$; or
nn) -hydrogen;

wherein T$_1$ and T$_2$ independently comprise —CH$_2$—, —O—, —N(R$_{15}$)—, —C(O)—, —CON(R$_{15}$)—, —N(R$_{15}$)C(O)—, —N(R$_{15}$)CON(R$_{16}$)—, —N(R$_{15}$)C(O)O—, —OC(O)N(R$_{15}$)—, —N(R$_{15}$)SO$_2$—, —SO$_2$N(R$_{15}$)—, —C(O)—O—, O—C(O)—, —S—, —S(O)—, —S(O$_2$)—, —N(R$_{15}$)SO$_2$N(R$_{16}$)—,

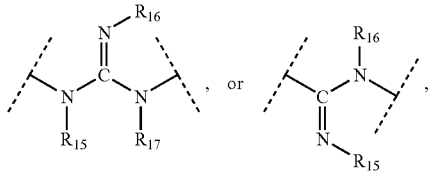

, or and wherein R$_{14}$, R$_{15}$, R$_{16}$ and R$_{17}$, independently comprise -hydrogen, -alkyl, -aryl, -arylene-alkyl, -alkylene-aryl, or -alkylene-arylene-alkyl. In another embodiment, Ar$_2$ may comprise a substituted phenyl, 2-naphthyl, 2-pyridyl, 3-isoquinolyl, 2-pyrimidyl or 2-quinazolyl group having 1 to 5 substituents independently comprising:
a) -fluoro;
b) -chloro;
c) -bromo;
d) -iodo;
e) -cyano;
f) -nitro;
g) -perfluoroalkyl;
h) -T$_1$-R$_{14}$;
i) -alkyl;
j) -aryl;
k) -arylene-alkyl;
l) -T$_1$-alkyl;
m) -T$_1$-alkylene-aryl;
n) -T$_1$-arylene-aryl;
o) -T$_1$-arylene-alkyl;
p) -T$_1$-aryl;
q) -T$_1$-alkylene-T$_2$-R$_{14}$
r) -T$_1$-arylene-T$_2$-R$_{14}$;
s) -T$_1$-alkylene-arylene-aryl;
t) -T$_1$-alkylene-arylene-alkyl; or
u) -arylene-T$_1$-alkyl;

wherein T$_1$ and T$_2$ independently comprise —CH$_2$—, —O—, —N(R$_{15}$)—, —CON(R$_{15}$)—, —N(R$_{15}$)C(O), —N(R$_{15}$)SO$_2$—, or —C(O)—O—; wherein R$_{14}$, and R$_{15}$, independently comprise: -hydrogen, -alkyl, or -aryl.

In one embodiment, Ar$_2$ and X together comprise: [bromo-(tert-butyl-benzenesulfonylamino)]-benzoylamino;(3'-chloro-4'-fluoro-4-hydroxy-biphenyl-3-carbonyl)-amino; (biphenyl-4-ylmethoxy)-benzoylamino; {chloro-[(naphthalen-1-ylmethyl)-amino]}-benzoylamino; [(bistrifluoromethyl-benzoylamino)-bromo]-benzoylamino; {chloro-[(naphthalen-1-ylmethyl)-amino]}-benzoylamino; [(naphthalen-1-ylmethyl)-amino]-benzoylamino; [chloro-(carboxyhexylamino)]-benzoylamino; {chloro-[(dimethylamino-naphthalene)-sulfonylamino]}-benzoylamino; [chloro-(2-methyl-pentylamino)]-benzoylamino; [(biphenyl-sulfonylamino)-chloro]-benzoylamino; [chloro-(2-methyl-butylamino)]-benzoylamino; {chloro-[N-(carboxyhexyl)-N'-( bis-trifluoromethyl-benzoyl)-amino)]}-benzoylamino; or {[N-(bis-trifluoromethyl-benzoyl)-N'-pentylamino]-chloro}-benzoylamino.

The alkyl, aryl, heteroaryl, alkylene, and arylene groups in Ar$_1$, Ar$_2$, and R$_1$—R$_{17}$ may be optionally substituted 1 to 4 times with a substituent group, wherein said substituent group(s) or the term substituted refers to groups comprising:
a) -hydrogen;
b) -fluoro;
c) -chloro;
d) -bromo;
e) -iodo;
f) -cyano;
g) -nitro;
h) -perfluoroalkyl;
i) -Q-R$_{18}$;
j) -Q-alkyl;
k) -Q-aryl;
l) -Q-alkylene-aryl;
m) -Q-alkylene-NR$_{19}$R$_{20}$; or
n) -Q-alkyl-W—R$_{21}$;
wherein Q and W independently comprise: —CH$_2$—, —O—, —N(R$_{22}$)—, —C(O)—, —CON(R$_{22}$)—, —N(R$_{22}$)C(O)—, —N(R$_{22}$)CON(R$_{23}$)—, —N(R$_{22}$)C(O)O—, —OC(O)N(R$_{22}$)—, —N(R$_{22}$)SO$_2$—, —SO$_2$N(R$_{22}$)—, —C(O)—O—, —O—C(O)—, or —N(R$_{22}$)SO$_2$N(R$_{23}$)—, wherein R$_{18}$, R$_{19}$, R$_{20}$, R$_{21}$, R$_{22}$, and R$_{23}$, independently comprise: -hydrogen, -alkyl, -aryl, -arylene-alkyl, -alkylene-aryl, or -alkylene-arylene-alkyl.

Also included within the scope of the invention are the individual enantiomers of the compounds represented by Formula (I) above as well as any wholly or partially racemic mixtures thereof. The present invention also covers the individual enantiomers of the compounds represented by formula above as mixtures with diastereoisomers thereof in which one or more stereocenters are inverted.

In one group of example embodiments, the compounds are represented by Formula (I), in which c is equal to 0; G comprises -hydrogen or —CO$_2$H; V comprises —CH$_2$— or a direct bond; X comprises —N(R$_8$)—, —N(R$_8$)CO—, or —CO(NR$_8$)— wherein R$_8$ comprises -hydrogen; Ar$_1$ comprises a mono-substituted phenyl group, wherein the substituent comprises -aryl, -arylene-alkyl, -D-aryl, -D-alkylene-arylene-alkyl, -arylene-D-alkyl, -arylene-D-R$_{10}$, or -D-alkylene-arylene-aryl, wherein R$_{10}$ comprises -aryl, or -alkylene-aryl, and D comprises -O-, or -N(R$_{11}$)—, wherein R$_{11}$ comprises -hydrogen, -alkyl, or -aryl; and Ar$_2$ comprises a substituted phenyl, 2-naphthyl, 2-pyridyl, 3-isoquinolyl, 2-pyrimidyl or 2-quinazolyl group having 1 to 5 substituents independently comprising -hydrogen, -fluoro, -chloro, -bromo, iodo, -cyano, -nitro, -perfluoroalkyl, -T$_1$-R$_{14}$, -alkyl, -aryl, -arylene-alkyl, -T$_1$-alkyl, -T$_1$-alkylene-aryl, -T$_1$-arylene-aryl, -T$_1$-arylene-alkyl, -T$_1$-aryl, T$_1$-alkyleneT$_2$-R$_{14}$, -T$_1$-alkyleneT$_2$-R$_{14}$, -T$_1$-alkylene-arylene-aryl, -T$_1$-alkylene-arylene-alkyl, or -arylene-T$_1$-alkyl; wherein T$_1$ and T$_2$ independently comprise —CH$_2$—, —O—, —N(R$_{15}$)—, —CON(R$_{15}$)—, —N(R$_{15}$)C(O)—, —N(R$_{15}$)SO$_2$—, or —C(O)—O—; wherein R$_{14}$ and R$_{15}$ independently comprise -hydrogen, -alkyl, or -aryl.

Example compounds of the present invention are listed by name below in Table 1.

TABLE 1

| Example | Structure | Chemical Name |
|---|---|---|
| 1 | 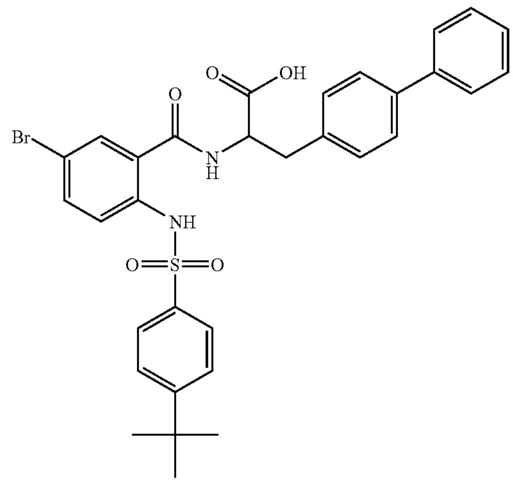 | 3-biphenyl-4-yl-2-[5-bromo-2-(4-tert-butyl-benzenesulfonylamino)-benzoyl-amino]-propionic acid |
| 2 | 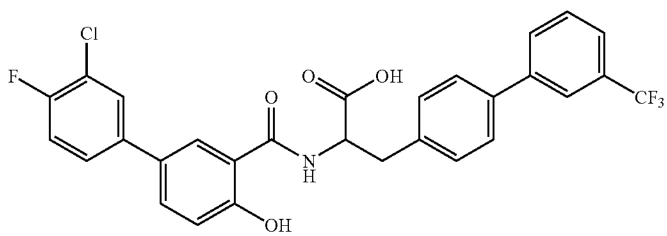 | (2S)-[(3'-chloro-4'-fluoro-4-hydroxy-biphenyl-3-carbonyl)-amino]-3-(3'-trifluoromethyl-biphenyl-4-yl)-propionic acid |
| 3 | 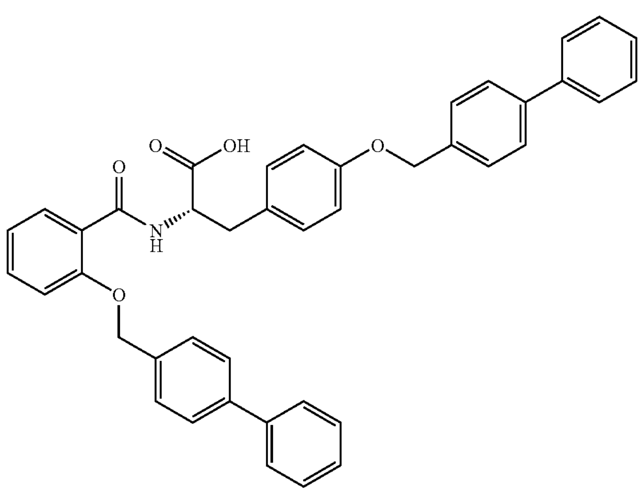 | (2S)-[2-(biphenyl-4-ylmethoxy)-benzoylamino]-3-[4-(biphenyl-4-ylmethoxy)-phenyl]-propionic acid |

TABLE 1-continued

| Example | Structure | Chemical Name |
|---|---|---|
| 4 | 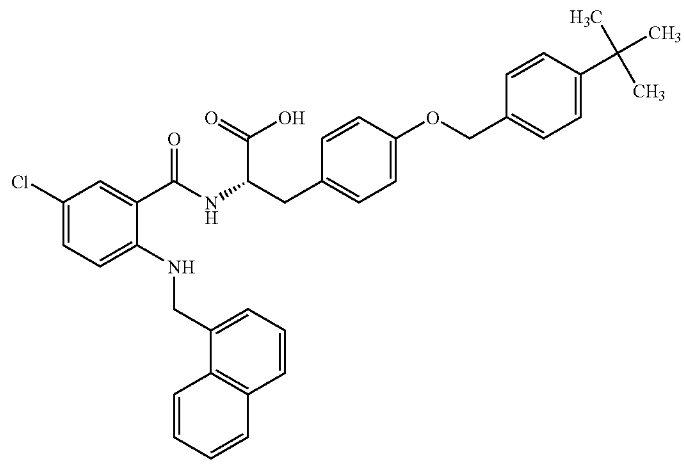 | (2S)-3-[4-(4-tert-butyl-benzyloxy)-phenyl]-2-{5-chloro-2-[(naphthalen-1-yl-methyl)-amino]-benzoylamino}-propioinic acid |
| 5 | 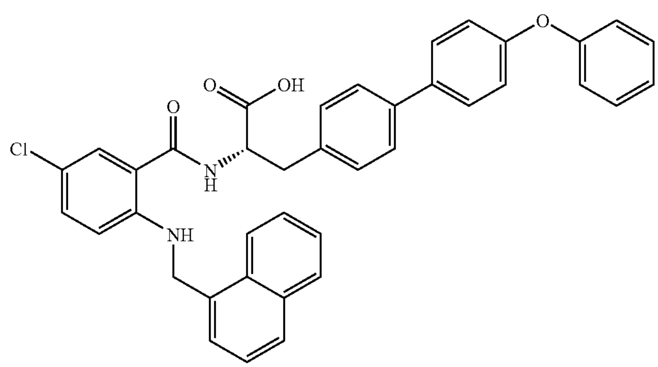 | (2S)-{5-chloro-2-[(naphthalen-1-yl-methyl)-amino]-benzoylamino}-3-(4'-phenoxy-biphenyl-4-yl)-propionic acid |
| 6 | 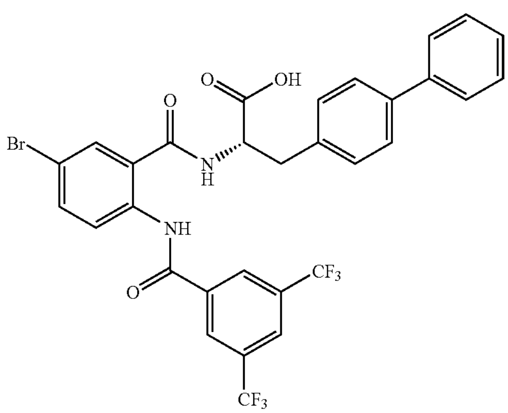 | 3-biphenyl-4-yl-(2S)-[2-3,5-bis-trifluoromethyl-benzoylamino)-5-bromo-benzoylamino]-propionic acid |
| 7 | 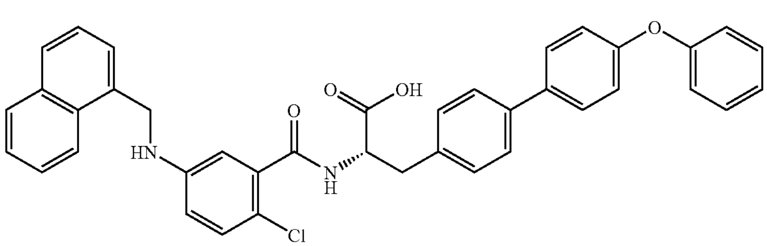 | (2S)-{2-chloro-5-[(naphthalen-1-yl-methyl)-amino]-benzoylamino}-3-(4'-phenoxy-biphenyl-4-yl)-propioinic acid |

TABLE 1-continued

| Example | Structure | Chemical Name |
|---|---|---|
| 8 | 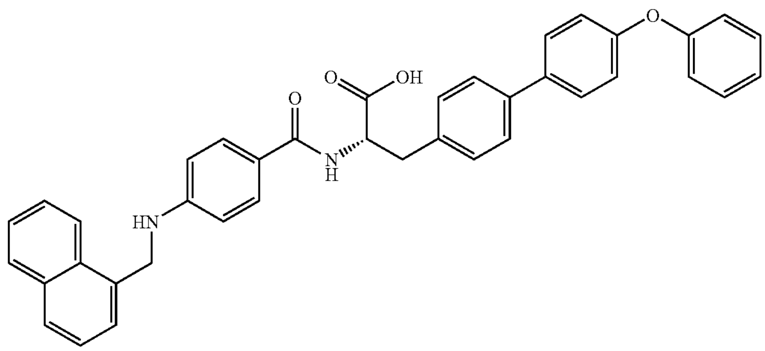 | (2S)-{4-[(naphthalen-1-ylmethyl)-amino-benzoylamino}-3-(4'-phenoxy-biphenyl-4-yl)-propionic acid |
| 9 | 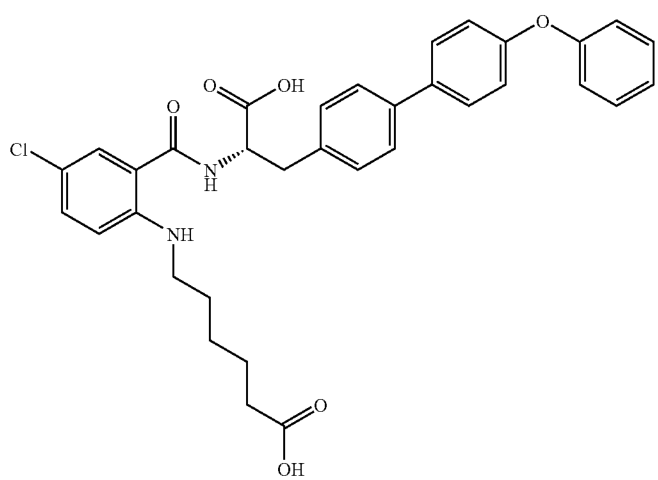 | 6-{(2S)-[1-carboxy-2-(4'-phenoxy-biphenyl-4-yl)-ethylcarbamoyl]-4-chloro-phenylamino}-hexanoic acid |
| 10 | 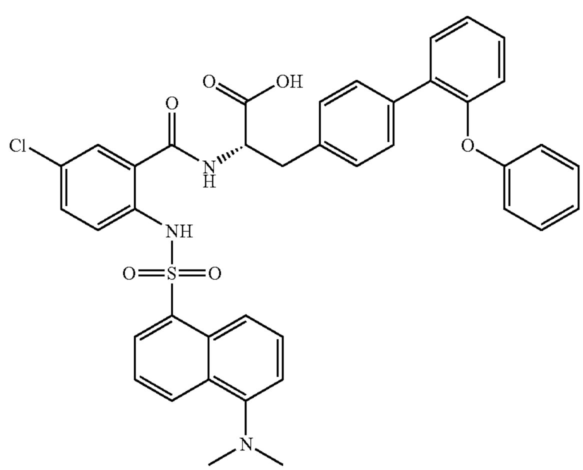 | (2S)-[5-chloro-2-(5-dimethylamino-naphthalene-1-sulfonylamino)-benzoylamino]-3-(2'-phenoxy-biphenyl-4-yl)-propionic acid |

TABLE 1-continued

| Example | Structure | Chemical Name |
| --- | --- | --- |
| 11 | 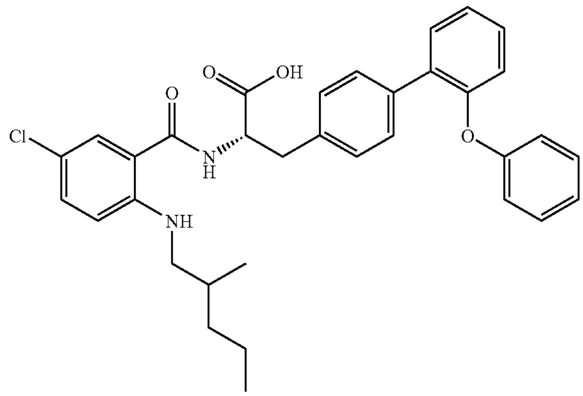 | (2S)-[5-chloro-2-(2-methyl-pentyl-amino)-benzoylamino]-3-(2'-phenoxy-biphenyl-4-yl)-propionic acid |
| 12 | 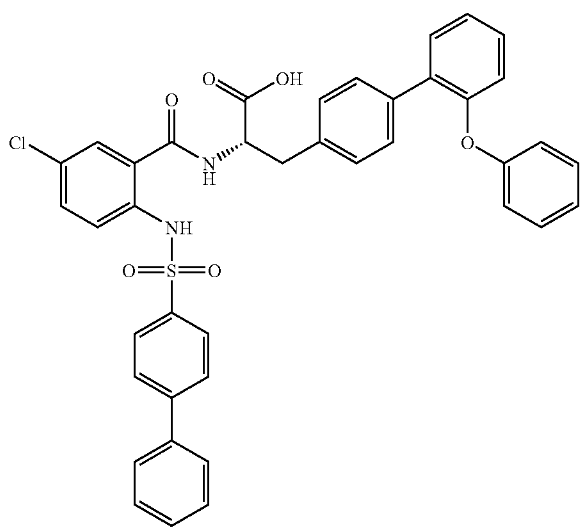 | (2S)-[2-(biphenyl-4-sulfonylamino)-5-chloro-benzoylamino]-3-(2'-phenoxy-biphenyl-4-yl)-propionic acid |
| 13 | 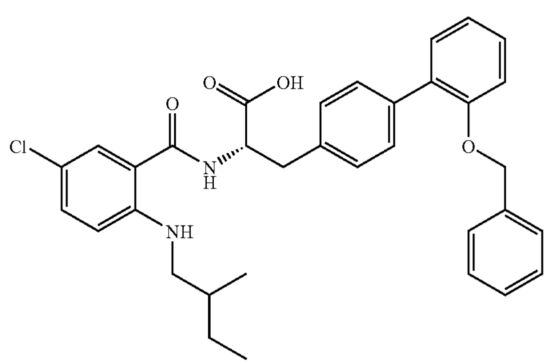 | 3-(2'-benzyloxy-biphenyl-4-yl)-(2S)-[5-chloro-2-(2-methyl-butylamino)-benzoylamino]-propionic acid |

TABLE 1-continued

| Example | Structure | Chemical Name |
|---|---|---|
| 14 | 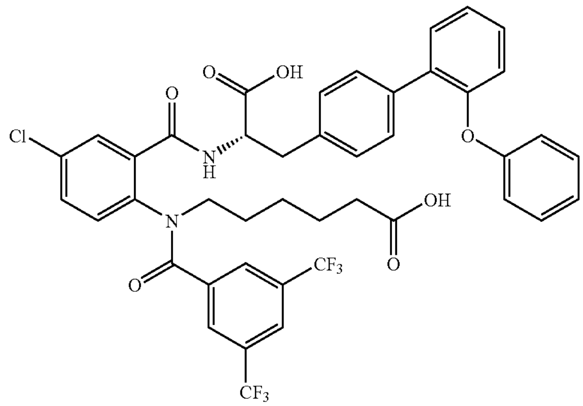 | 6-((3,5-bis-trifluoro-methyl-benzoyl)-{(2S)-[1-carboxy-2-(2'-phenoxy-biphenyl-4-yl)-ethylcarbamoyl]-4-chloro-phenylamino}-hexanoic acid |
| 15 | 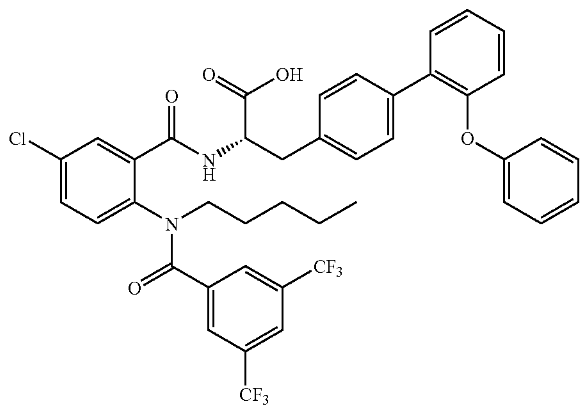 | (2S)-2-[((3,5-bis-trifluoromethyl-benzoyl)-pentyl-amino]-5-chloro-benzoyl-amino]-3-(2'-phenoxy-biphenyl-4-yl)-propionic acid |

Unless indicated otherwise, the structures of the Examples of compounds of Formula (I) having vacant connectivity for heteroatoms, such as oxygen and nitrogen, are assumed to have a hydrogen atom attached thereto.

In another aspect, the present invention provides a pharmaceutical composition comprising a compound of Formula (I) and one or more pharmaceutically acceptable carriers, excipients, or diluents.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may containing one or more O, S, S(O), or S(O)$_2$ atoms. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may containing one or more O, S, S(O), or S(O)$_2$ atoms. Examples of "alkylene" as used herein include, but are not limited to, methylene, ethylene, and the like.

As used herein, "cycloalkyl" refers to a alicyclic hydrocarbon group optionally possessing one or more degrees of unsaturation, having from three to twelve carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally possessing one or more degrees of unsaturation, containing one or more heteroatomic substitutions selected from S, SO, SO$_2$, O, or N, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, SO$_2$, O, or N, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

As used herein, the term "aryl" refers to a benzene ring or to an optionally substituted benzene ring system fused to one or more optionally substituted benzene rings, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five-to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five-to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-dily, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

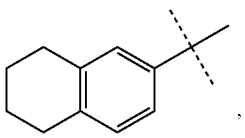

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl,

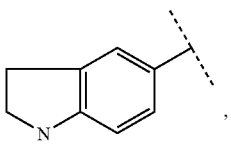

and the like

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

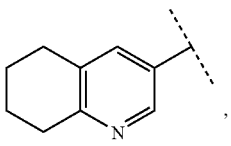

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include 1,2,3,4-tetrahydro-beta-carbolin-8-yl,

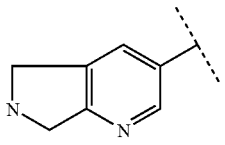

and the like.

As used herein, the term "acid isostere" refers to a substituent group which will ionize at physiological pH to bear a net negative charge. Examples of such "acid isosteres" include but are not limited to heteroaryl groups such as but not limited to isoxazol-3-ol-5-yl, 1H-tetrazole-5-yl, or 2H-tetrazole-5-yl. Such acid isosteres include but are not limited to heterocyclyl groups such as but not limited to imidazolidine-2,4-dione-5-yl, imidazolidine-2,4-dione-1-yl, 1,3-thiazolidine-2,4-dione-5-yl, 5-hydroxy-4H-pyran-4-on-2-yl, 1,2,5-thiadiazolidin-3-one-1,1-dioxide-4-yl, or 1,2,5-thiadiazolidin-3-one-1,1-dioxide-5-yl.

As used herein, the term "direct bond", where part of a structural variable specification, refers to the direct joining of the substituents flanking (preceding and succeeding) the variable taken as a "direct bond".

As used herein, the term "alkoxy" refers to the group $R_aO-$, where $R_a$ is alkyl.

As used herein, the term "acyl" refers to the group $R_aC(O)-$, where $R_a$ is alkyl, alkenyl, alkynyl, cycloalkyl, cycloalkenyl, or heterocyclyl.

As used herein, the term "aroyl" refers to the group $R_aC(O)-$, where $R_a$ is aryl.

As used herein, the term "heteroaroyl" refers to the group $R_aC(O)-$, where $R_a$ is heteroaryl.

As used herein, the term "alkoxycarbonyl" refers to the group $R_aOC(O)-$, where $R_a$ is alkyl.

As used herein, the term "acyloxy" refers to the group $R_aC(O)O-$, where $R_a$ is alkyl, alkenyl, alkynyl, cycloalkyl, cycloalkenyl, or heterocyclyl.

As used herein, the term "aroyloxy" refers to the group $R_aC(O)O-$, where $R_a$ is aryl.

As used herein, the term "heteroaroyloxy" refers to the group $R_aC(O)O-$, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, $-CH_2-O-CH_2-$, $-CH_2-SO_2-CH_2-$, $-CH_2-NH-H_3$ and so forth.

As used herein, the term "solvate" is a complex of variable stoichiometry formed by a solute (in this invention, a compound of Formula (I)) and a solvent. Such solvents for the purpose of the invention may not sunstantially interfere with the biological activity of the solute. Solvents may be, by way of example, water, ethanol, or acetic acid.

As used herein, the term "biohydrolyzable ester" is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to Formula (I) in plasma. Many examples of such are known in the art and include by way of example lower alkyl esters (e.g., $C_1$-$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to Formula (I) in plasma. Many examples of such are known in the art and include by way of example lower alkyl amides, alpha-amino acid amides, alkoxyacyl amides, and alkylaminoalkylcarbonyl amides.

As used herein, the term "prodrug" includes biohydrolyzable amides and biohydrolyzable esters and encompasses a) compounds in which the biohydrolyzable functionality in such a prodrug is encompassed in the compound of formula (I) and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like.

Whenever the terms "alkyl" or "aryl" or either of their prefix roots appear in a name of a substituent (e.g. arylalkoxyaryloxy) they shall be interpreted as including those limitations given above for "alkyl" and "aryl". Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

The present invention also provides a method for the synthesis of compounds useful as intermediates in the preparation of compounds of Formula (I) along with methods for the preparation of compounds of Formula (I). The compounds can be prepared according to the following reaction Schemes and procedures in which variables are as defined. In these reactions, it is also possible to make use of variants which are themselves known to those of ordinary skill in this art, but are not mentioned in greater detail.

Scheme I describes the synthesis of an intermediate of structure (4). $Ar_3$ and $Ar_4$ are, independently, groups such as, but not limited to, a heteroaryl or aryl ring system. As shown in Scheme I, in one embodiment, bromo- or iodo-substituted aryl alanine methyl ester (or amino acid esterified in linkage to Wang resin) (1) is treated with a carboxylic acid in the presence of a coupling reagent, such as, but not limited to, diisopropyl carbodiimide (DIC) to form the amide (2). The resulting amide is then subjected to coupling with an arylboronic acid in the presence of a catalyst such as but not limited to tetrakis(triphenylphosphine)palladium (0), in the presence of base such as, but not limited to, sodium carbonate to form compound (3). The methyl ester (3) is hydrolyzed using a base such as, but not limited to, LiOH to provide the free carboxylic acid (4), where $Ar_1$ and $Ar_2$ are as defined for Formula (I).

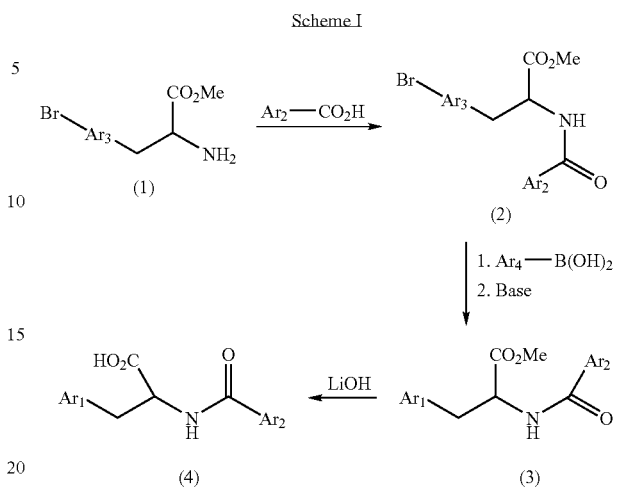

Scheme II describes the preparation of a compound of structure (4). $Ar_3$ and $Ar_4$ are, independently, groups such as but not limited to a heteroaryl or aryl ring system. As shown in Scheme II, in another embodiment, an aryl hydroxy amino acid methyl ester (or amino acid esterified in linkage to Wang resin) (5) is treated with a carboxylic acid $Ar_2$—$CO_2H$ in the presence of a coupling reagent such as, but not limited to, diisopropyl carbodiimide (DIC) to form the amide (6). The resulting amide is then subjected to: 1) nucleophilic substitutions with an optionally substituted electron—deficient fluoroaromatic or fluoroheteroaromatic in the presence of base such as, but not limited to, potassium carbonate; or 2) coupling with an aryl bromide, or heteroaryl bromide, and copper iodide in the presence of a base including, but not limited to, cesium carbonate to form compound (7). The methyl ester in (7) is hydrolyzed using a base such as LiOH to provide the free carboxylic acid (4), where $Ar_1$ and $Ar_2$ are as defined for Formula (I).

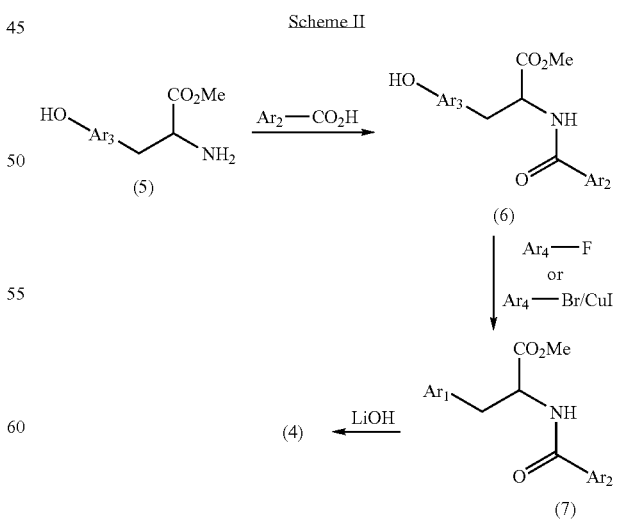

Scheme III describes the preparation of a compouind of formula (4). $Ar_5$ and $Ar_6$ are, independently, groups such as but not limited to a heteroaryl or aryl ring system. As shown in Scheme II, in another embodiment, an amino acid methyl ester (or, alternately, an amino acid esterified in linkage to Wang resin) (8) is treated with a bromo-substituted aryl carboxylic acid in the presence of a coupling reagent such as, but not limited to, diisopropyl carbodiimide (DIC) to form the amide (9). The resulting amide then is subjected to coupling with an arylboronic acid or heteroarylboronic acid in the presence of a catalyst such as but not limited to tetrakis(triphenylphosphine)palladium(0), in the presence of base such as, but not limited to, sodium carbonate to form compound (10). The methyl ester (10) is hydrolyzed using a base such as, but not limited to, LiOH to provide the free carboxylic acid (4), where $Ar_1$ and $Ar_2$ are as defined for Formula (I).

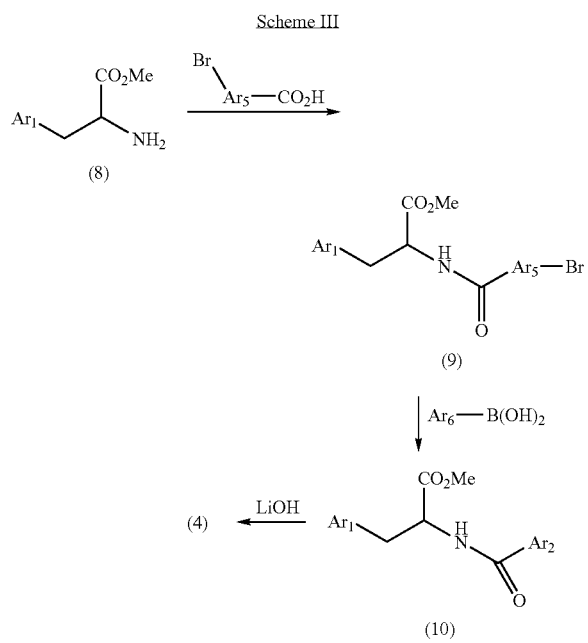

Scheme IV describes the synthesis of a compound of formula (4). $Ar_3$, $Ar_7$, $Ar_5$ and $Ar_6$ are, independently, groups such as but not limited to a heteroaryl or aryl ring system. As shown in Scheme IV, in another embodiment, a bromo or iodo aryl alanine methyl ester (or amino acid esterified in linkage to Wang resin) (11) is subjected to coupling with an arylboronic acid in the presence of a catalyst such as but not limited to tetrakis(triphenylphosphine)palladium(0), in the presence of base such as but not limited to sodium carbonate to form compound (12). The resulting compound is treated with a bromo- or iodo-substituted aryl carboxylic acid in the presence of a coupling reagent such as, but not limited to, diisopropyl carbodiimide (DIC) to form the amide (13). The resulting amide is then subjected to coupling with a arylboronic acid or heteroarylboronic acid in the presence of a catalyst such as but not limited to tetrakis(triphenylphosphine)plladium(0), in the presence of base such as, but not limited to, sodium carbonate, and the product methyl ester is hydrolyzed using a base such as LiOH to provide the free carboxylic acid (4), where $Ar_1$ and $Ar_2$ are as defined for Formula (I).

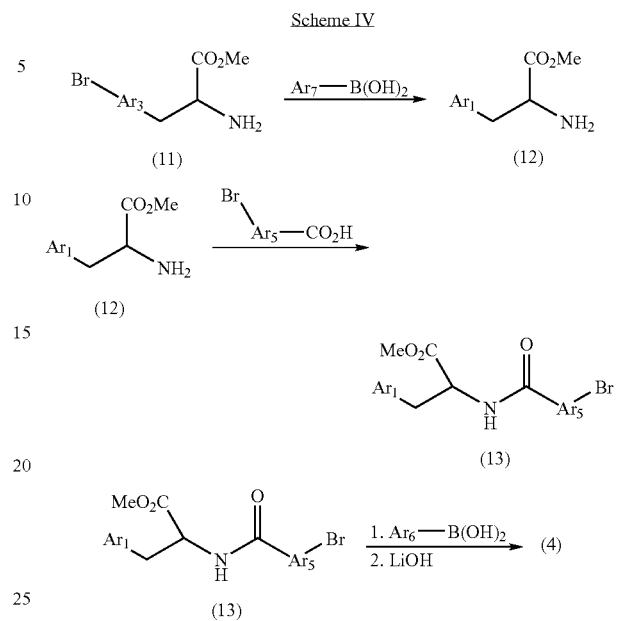

Scheme V describes the preparation of a compound of formula (16). $Ar_3$ and $Ar_7$ are, independently, groups such as but not limited to a heteroaryl or aryl ring system. Pol is a functionalized polymeric support, such as but not limited to Wang Resin. As shown in Scheme V, in another embodiment, a hydroxy aryl ester loaded onto the Wang Bromo resin or Merrifield resin using base such as, but not limited to, sodium methoxide in DMA, and hydrolyzed to give (14), is coupled with a bromo- or iodo-subsituted aryl amino acid methyl ester (11) in the presence of a coupling reagent such as, but not limited to, diisopropyl carbodiimide (DIC) to give the amide (15). The resulting amide (15) is then subjected to a coupling with an arylboronic acid or heteroarylboronic acid in the presence of a catalyst such as but not limited to tetrakis(triphenylphosphine)palladium(0), in the presence of base such as, but not limited to, sodium carbonate followed by cleavage from the resin with TMSBr/TFA/DCM (1:1:1) or a similar suitable cleavage cocktail to yield the desired product (16), where $Ar_1$ and $Ar_2$ are as defined for Formula (I).

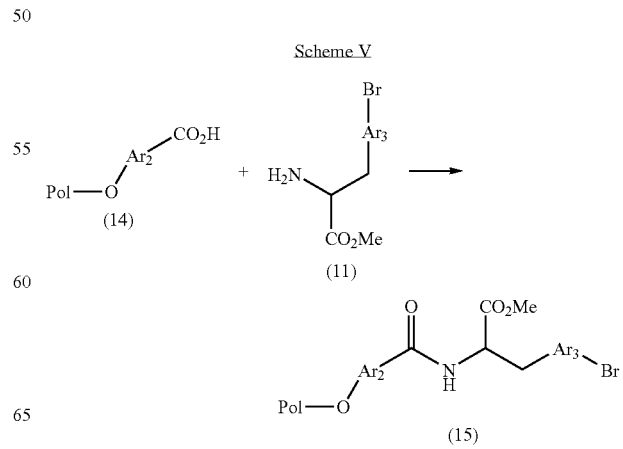

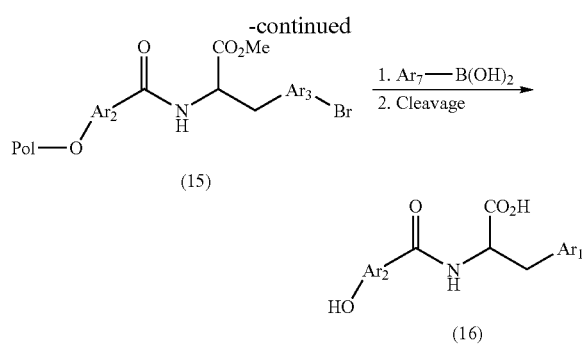

Scheme VI describes the preparation of a compound of formula (19). Ar₆ and Ar₈ are, independently, groups such as but not limited to a heteroaryl or aryl ring system. Pol is a functionalized polymeric support, such as but not limited to Wang Resin. As shown in Scheme VI, in another embodiment, a hydroxy aryl ester loaded onto the Wang Bromo resin, Merrifiend resin, or other suitable support using base such as, but not limited to, sodium methoxide in DMA, is hydrolyzed to give (17), and is coupled with an amino acid methyl ester (8) in the presence of a coupling reagent such as, but not limited to, diisopropyl carbodiimide (DIC) to give the amide (18). The resulting amide (18) is then subjected to a coupling with an arylboronic acid or heteroarylboronic acid in the presence of a catalyst such as but not limited to tetrakis(triphenylphosphine)palladium(0), in the presence of base such as, but not limited to, sodium carbonate, and is then cleaved from the resin with TMSBr/TFA/DCM (1:1:1) or a similar suitable cleavage cocktail to yield the desired product (19), where $Ar_1$ and $Ar_2$ are as defined for Formula (I).

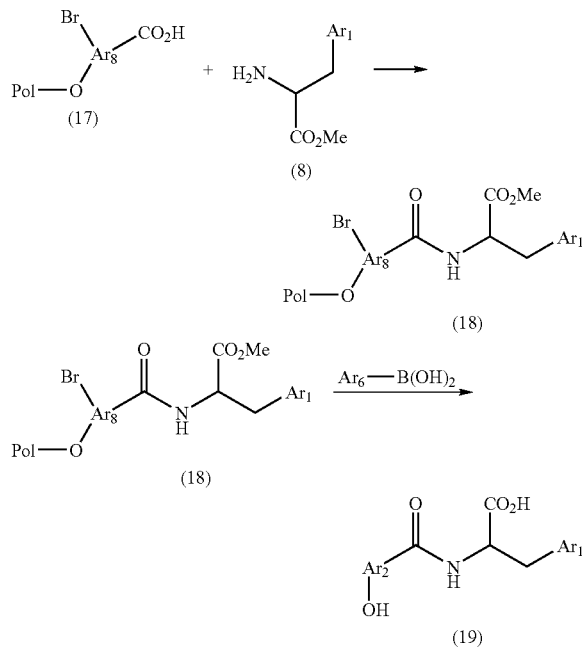

Scheme VII describes the synthesis of a compound of formula (23). Ar₃, Ar₇, and Ar₆ are, independently, groups such as but not limited to a heteroaryl or aryl ring system. Pol is a functionalized polymeric support, such as but not limited to Wang Resin. As shown in Scheme VII, in another embodiment, a bromo hydroxy aryl ester (20) loaded onto Wang Bromo resin, Merrifield resin, or other suitable support using base such as, but not limited to, sodium methoxide in DMF, is then subjected to a coupling with an arylboronic acid or heteroarylboronic acid in the presence of a catalyst such as but not limited to tetrakis(triphenylphosphine)plladium(0), in the presence of base such as, but not limited to, sodium carbonate, followed by hydrolysis of the product ester to yield the acid (21). The resulting carboxylic acid (21) is then subjected to coupling with a bromo- or iodo-substituted aryl amino acid methyl ester (11) in the presence of a coupling reagent such as, but not limited to, diisopropyl carbodiimide (DIC) to give the amide (22). The resulting amide (22) is then subjected to a coupling with an arylboronic acid or heteroaryl boronic acid in the presence of a catalyst such as but not limited to tetrakis(triphenylphosphine)plladium(0), in the presence of base such as, but not limited to, sodium carbonate followed by cleavage from the resin with TMSBr/TFA/DCM (1:1:1) or a similar cleavage cocktail to yield the desired product (23), where $Ar_1$ and $Ar_2$ are as defined for Formula (I).

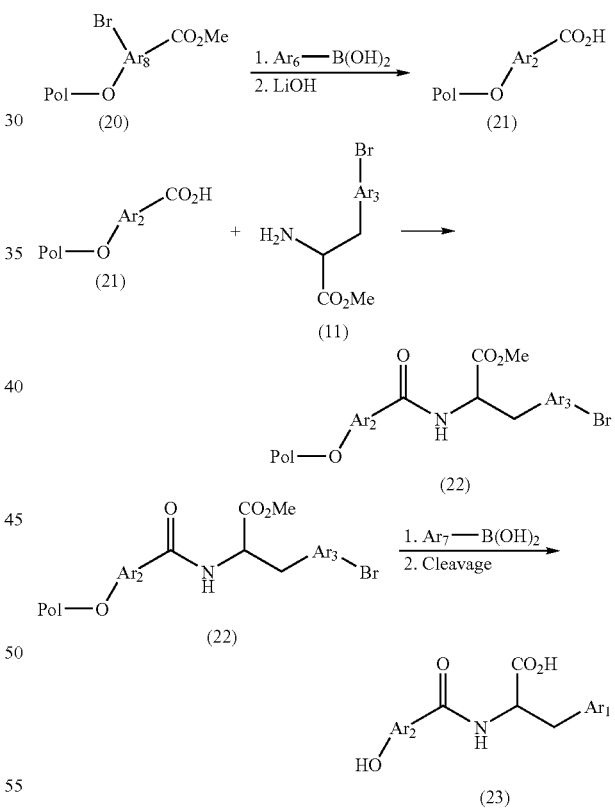

Scheme VIII describes the preparation of a compound of formula (29). Ar₇, Ar₉, Ar₁₀, and Ar₁₁ are, independently, groups such as but not limited to a heteroaryl or aryl ring system. As shown in Scheme VIII, in another embodiment, a fluoro nitro phenol (24) loaded onto a polymer such as Wang Bromo resin using base such as, but not limited to, sodium methoxide in DMA, is then treated with a hydroxy aryl compound (25) in the presence of base, followed by reduction of the nitro group to give the free amine (26). The resulting amine (26) is then subjected to coupling with a bromo- or iodo-substituted aryl acid (27) in the presence of a coupling reagent such as, but not limited to, diisopropyl carbodiimide (DIC) to give the amide (28). The resulting amide (28) is then subjected to a coupling with an arylboronic acid or heteroarylboronic acid in the presence of a catalyst such as but not limited to tetrakis(triphenylphosphine)palladium(0), in the presence of base such as, but not limited to, sodium carbonate followed by cleavage from the resin with TMSBr/TFA/DCM (1:1:1) or a similar suitable cleavage cocktail to yield the desired product (29), where $Ar_1$ and $Ar_2$ are as defined for Formula (I).

of the product methyl ester with an alkaline reagent such as LiOH provides compound (32), where $Ar_1$ and $Ar_2$ are as defined for Formula (I).

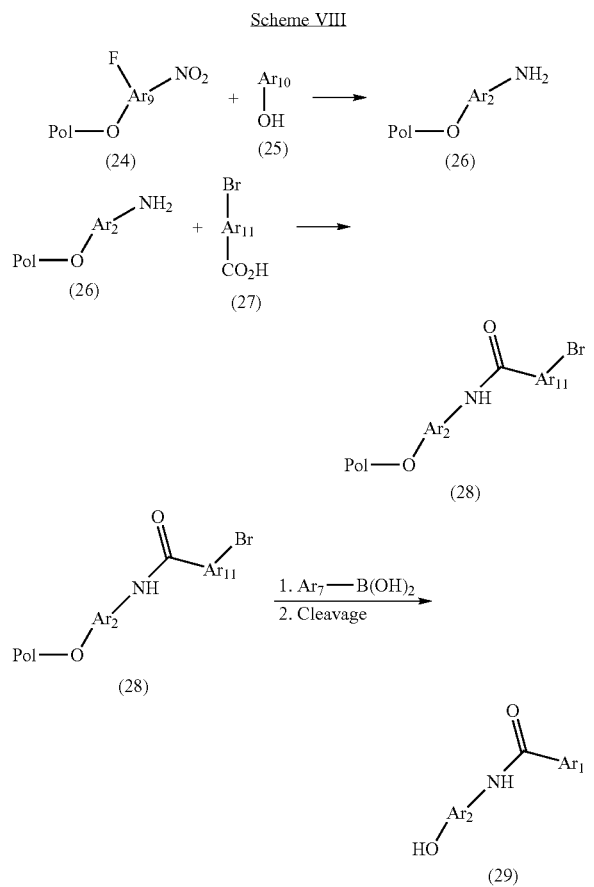

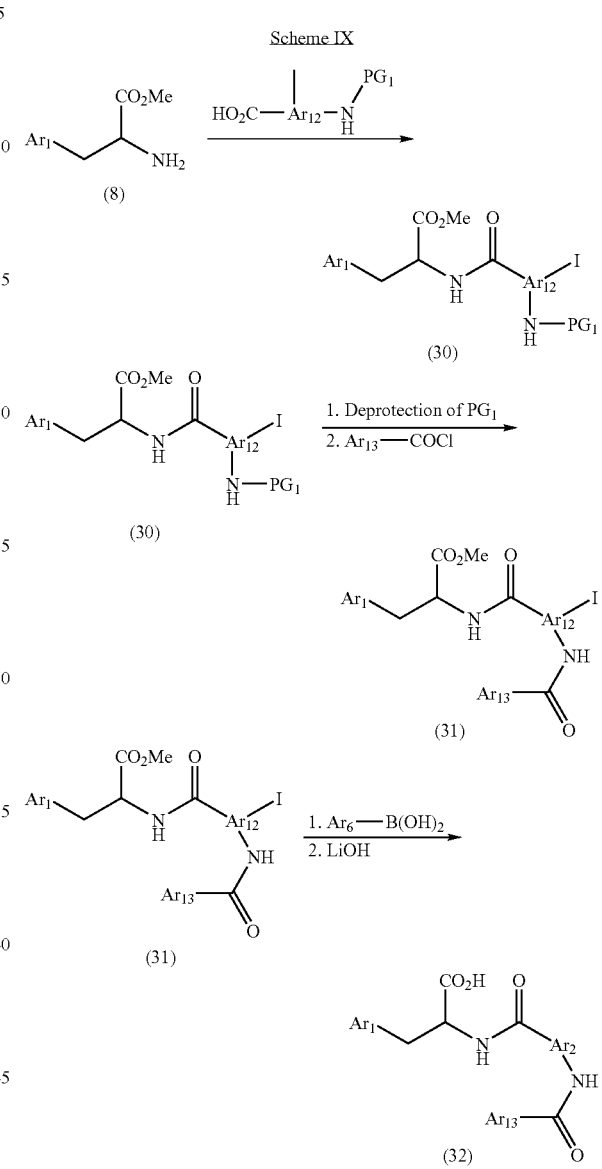

Scheme IX describes the preparation of a compound of formula (32). $Ar_6$, $Ar_{12}$, and $Ar_{13}$ are, independently, groups such as but not limited to a heteroaryl or aryl ring system. $PG_1$ is an amino protecting group such as allyloxycarbonyl or tert-butoxycarbonyl. As shown in Scheme IX, in another embodiment, an aryl amino acid methyl ester (8) is reacted with an iodo-subsituted aryl amino carboxylic acid (the amino group of which may be protected with an amino protecting group $PG_1$ in the presence of a coupling reagent such as, but not limited to, diisopropyl carbodiimide (DIC) giving the amide (30). The amino group of the amide (30) may be then deprotected, if desired, by treatment with, in the case of $PG_1$ as tert-butoxycarbonyl, TFA, and is then treated with an aroyl chloride in the presence of a base such as pyridine or TEA to give the iodo amide (31). The amide (31) is subjected to coupling with an arylboronic acid or heteroaryl boronic acid in the presence of a catalyst such as but not limited to tetrakis(triphenylphosphine)palladium(0), in the presence of base such as, but not limited to, sodium carbonate. Hydrolysis The term "amino protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. In one embodiment, amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. The related term "protected amino" or "protected amino group" defines an amino group substituted with an amino-protecting group discussed above.

The term "hydroxyl protecting group" as used herein refers to substituents of the alcohol group commonly employed to block or protect the alcohol functionality while reacting other functional groups on the compound. Examples of such alcohol-protecting groups include the 2-tetrahydropyranyl group, 2-ethoxyethyl group, the trityl group, the trichloroacetyl group, urethane-type blocking groups such as benzyloxycarbonyl, and the trialkylsilyl group, examples of such being trimethylsilyl, tert-butyldimethylsilyl, phenyldimethylsilyl, triiospropylsilyl and thexyldimethylsilyl. The choice of alcohol-protecting group employed is not critical so long as the derivatized alcohol group is stable to the condition of subsequent reaction(s) on other positions of the compound of the formulae and can be removed at the desired point without disrupting the remainder of the molecule. The related term "protected hydroxyl" or "protected alcohol" defines a hydroxyl group substituted with a hydroxyl-protecting group as discussed above.

The term "carboxyl protecting group" as used herein refers to substituents of the carboxyl group commonly employed to block or protect the —OH functionality while reacting other functional groups on the compound. Examples of such alcohol-protecting groups include the 2-tetrahydropyranyl group, 2-ethoxyethyl group, the trityl group, the allyl group, the trimethylsilylethoxymethyl group, the 2,2,2-trichloroethyl group, the benzyl group, and the trialkylsilyl group, examples of such being trimethylsilyl, tert-butyldimethylsilyl, phenyldimethylsilyl, triiospropylsilyl and thexyldimethylsilyl. The choice of carboxyl protecting group employed is not critical so long as the derivatized alcohol group is stable to the condition of subsequent reaction(s) on other positions of the compound of the formulae and can be removed at the desired point without disrupting the remainder of the molecule. The related term "protected carboxyl" defines a carboxyl group substituted with a carboxyl -protecting group as discussed above.

Further examples of the protecting groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981.

In another aspect, the present invention provides a pharmaceutical composition comprising a compound of Formula (I). Thus, the invention further provides pharmaceutical compositions comprising erythropoietin receptor activating compounds of the invention. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques. The term "treatment" as used herein, refers to the full spectrum of treatments for a given disorder from which the patient is suffering, including alleviation of one, most of all symptoms resulting from that disorder, to an outright cure for the particular disorder or prevention of the onset of the disorder. The term "EPO" is used herein to refer to erythropoietin.

The term "therapeutically effective amount" is used herein to denote that amount of a drug or pharmaceutical agent that will elicit the therapeutic response of an animal or human that is being sought. In one embodiment, a therapeutically effective amount of the compound of Formula (I) comprises an amount sufficient to treat a disease mediated at least in part by an erythropoietin receptor.

Pharmaceutical compositions comprising a compound of Formula (I) may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. The tablets may also be coated by the techniques described in U.S. Pat. Nos. 4,356,108; 4,166,452; and 4,265,874, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; or dispersing or wetting agents, as for example, a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient, which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include eyedrops, mouth washes, and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Also provided by the present invention are prodrugs of the invention.

Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Methanesulfonate, Methylbromide, Methyinitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

Other salts which are not pharmaceutically acceptable may be useful in the preparation of compounds of the invention and these form a further aspect of the invention.

In addition, some of the compounds of Formula (I) may form solvates with water or common organic solvents. Such solvates are also encompassed within the scope of the invention.

Thus, in another aspect of the present invention, there is provided a pharmaceutical composition comprising a therapeutically effective amount of a compound of Formula (I), or a pharmaceutically acceptable salt, solvate, or prodrug therof, and one or more pharmaceutically acceptable carriers, excipients, or diluents. In an embodiment of the pharmaceutical composition, the compound of Formula (I) is a binder and activator of an erythropoietin receptor. In another embodiment of the pharmaceutical composition, the compound of Formula (I) induces red blood cell production mediated by erythropoietin receptor activation.

In another aspect of the present invention, there is provided a pharmaceutical composition comprising a therapeutically effective amount of a compound of Formula (I), or a pharmaceutically acceptable salt, solvate, or prodrug therof, and one or more pharmaceutically acceptable carriers, excipients, or diluents, wherein said therapeutically effective amount comprises a sufficient amount of the compound of Formula (I) to at least partially activate an erythropoietin receptor in a subject, a sufficient amount of the compound of Formula (I) for at least partial amelioration of at least one erythropoietin signal transduction related disease, a sufficient amount of the compound of Formula (I) to treat or ameliorate a disease mediated at least in part by an erythropoietin receptor in a subject, or a sufficient amount of the compound of Formula (I) to at least partially induce red blood cell production in a subject. In an embodiment of the pharmaceutial composition, the disease mediated at least in part by an erythropoietin receptor and/or the erythropoietin signal transduction related disease comprises anemia of renal failure. In another embodiment of the pharmaceutial composition, the disease mediated at least in part by an erythropoietin receptor and/or the erythropoietin signal transduction related disease comprises anemia of end-stage renal disease. In another embodiment of the pharmaceutial composition, the disease mediated at least in part by an erythropoietin receptor and/or the erythropoietin signal transduction related disease comprises anemia of chronic disorders, wherein the chronic disorders are associated with chronic infections and rheumatoid arthritis. In another embodiment of the pharmaceutial composition, the disease mediated at least in part by an erythropoietin receptor and/or the erythropoietin signal transduction related disease comprises anemia of autoimmune diseases. In another embodiment of the pharmaceutial composition, the disease mediated at least in part by an erythropoietin receptor and/or the erythropoietin signal transduction related disease comprises anemia of AIDS. In another embodiment of the pharmaceutial composition, the disease mediated at least in part by an erythropoietin receptor and/or the erythropoietin signal transduction related disease comprises anemia of malignancy.

In another aspect, the present invention provides a pharmaceutical composition comprising a therapeutically effective amount of the compound of Formula (I), and one or more pharmaceutically acceptable carriers, excipients, or diluents, wherein said pharmaceutical composition is used to replace or supplement compounds that induce red blood cell production.

The erythropoietin receptor activators of the invention may be used in adjuvant therapeutic or combination therapeutic treatments with other known therapeutic agents. In another embodiment, the present invention provides a pharmaceutical composition comprising a therapeutically effective amount of the compound of Formula (I), and one or more pharmaceutically acceptable carriers, excipients, or diluents, further comprising one or more therapeutic agents.

The following is a non-exhaustive listing of adjuvants and additional therapeutic agents which may be utilized in combination with the compounds of Formula I of the present invention:

Pharmacologic classifications of treatment for Diabetes Mellitus
1. Sulfonylureas: tolbutamide, tolazamide, glyburide, glipizide
2. Biguanides: Mefformin
3. Miscellaneous oral agents: acarbose, PPAR ligands such as but not limited to troglitazone, DPP-IV inhibitors, glucokinase activators
4. Insulin, insulin mimetics, insulin secretagogues, insulin sensitizers
5. GLP-1, GLP-1 mimetics Pharmacologic classifications of anticancer agents:
1. Alkylating agents: cyclophosphamide, nitrosoureas, carboplatin, cisplatin, procarbazine
2. Antibiotics: bleomycin, daunorubicin, doxorubicin
3. Antimetabolites: methotrexate, cytarabine, fluorouracil
4. Plant alkaloids: vinblastine, vincristine, etoposide, paclitaxel,
5. Hormones: tamoxifen, octreotide acetate, finasteride, flutamide
6. Biologic response modifiers: interferons, interleukins Pharmacologic classifications of treatment for inflammation, including rheumatoid arthritis
1. Analgesics: aspirin
2. NSAIDs (Nonsteroidal anti-inflammatory drugs): ibuprofen, naproxen, diclofenac
3. DMARDs (Disease-Modifying Antirheumatic drugs): methotrexate, gold preparations, hydroxychloroquine, sulfasalazine
4. Biologic Response Modifiers, DMARDs: etanercept, infliximab
5. Glucocorticoids Pharmacologic classifications of treatment for bacterial or viral infection
　1. gyrase inhibitors; ciprofloxacin
　2. beta lactam antibiotics; cefuroxime, amoxicillin, cephalexin, ceclor, meropenem, aztreonam
　3. miscellaneous antibiotics; linezolid, erythromycin, streptomycin, vancomycin, doxycycline, rifampin, isoniazid
　4. antifungal agents; terbinafine, fluconazole, ketoconazole, amphotericin B, griseofulvin
　5. antiviral agents
　　a. Antiviral agents for AIDS treatment; AZT, abacavir, ddC, ddI, d4T, 3TC, ZDV, tenofovir, nevirapine, pentafuside, amprenavir, fosamprenavir, indinavir, nelfinavir, ritonavir, saquanivir
　　b. Antiviral agents (general); lamivudine, foscarnet, acyclovir, cidofovir, ganciclovir, valaciclovir In a further embodiment, the present invention provides a method of treating or preventing erythropoietin signal transduction mediated diseases, the method comprising administering to a subject, a therapeutically effective amount of a compound of Formula (I) alone or in combination with therapeutic agents selected from the group consisting of sulfonylureas; biguanides; miscellaneous oral agents; insulin and insulin mimetics, secretagogues, and sensitizers; GLP-1 and GLP-1 mimetics; alkylating agents; antibiotics; antimetabolites; plant alkaloids; hormones; biologic response modifiers; analgesics; NSAIDs; DMARDs; glucocorticoids; gyrase inhibitors; beta lactam antibiotics; miscellaneous antibiotics; antifungal agents; and antiviral agents.

The dosage at which the compounds of Formula (I) are used may be varied depending upon the condition being treated, the size of the individual, pharmacokinetic parameters, and the individual compound. In one embodiment, the compound of Formula (I) may comprise a dosage such that the concentration of the compound of Formula (I) at the EPO receptor is about 1000 micromolar (μM) or less. In another embodiment, the compound of Formula (I) may comprise a dosage such that the concentration of compound at the EPO receptor is about 300 micromolar (µM) or less. In yet another embodiment, the compound of Formula (I) may comprise a dosage such that the concentration of compound at the EPO receptor is about 50 micromolar (µM) or less.

The compound of Formula (I) may be administered at a dosage level of from about 0.01 to 1000 mg/kg of the body weight of the subject being treated. In another embodiment, the dosage range is between 0.01 and 100 mg/kg. In another embodiment, the dosage range is between 0.5 to 10 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms will generally contain between from about 5 mg to about 500 mg of active ingredient. This dosage may be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

The present invention may be further understood by reference to the following non-limiting examples. Examples of compounds of the present invention and procedures that may be used in to prepare and identify useful compounds of the present invention are described below.

General Experimental:

LC-MS data was obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient was run from 25% B (97.5% acetonitrile, 2.5% water, 0.05% TFA) and 75% A (97.5% water, 2.5% acetonitrile, 0.05% TFA) to 100% B. The mass spectrometer used was a Micromass ZMD instrument. All data was obtained in the positive mode unless otherwise noted. $^1$H NMR data was obtained on a Varian 400 MHz spectrometer.

Common names and definitions for resin reagents used in the disclosure are;

| Merrifield | p-Chloromethyl polystyrene |
|---|---|
| Hydroxy-Merrifield | p-Hydroxymethyl polystyrene |
| Wang | (4-Hydroxymethyl)phenoxymethyl polystyrene |
| Wang carbonate | 4-(p-nitrophenyl carbonate) phenoxymethyl polystyrene |
| Rink Resin | 4-(2',4'-Dimethoxyphenyl-Fmoc-aminomethyl)-phenoxy polystyrene resin |
| Wang Bromo Resin | (4-Bromomethyl)phenoxymethyl polystyrene |
| THP Resin | 3,4-Dihydro-2H-pyran-2-ylmethoxymethyl polystyrene |

Aldehyde resin can refer to the following:
  4-Benzyloxybenzaldehyde polystyrene;
  3-Benzyloxybenzaldehyde polystyrene;
  4-(4-Formyl-3-methoxyphenoxy)butyryl-aminomethyl polystyrene;
  2-(4-Formyl-3-methoxyphenoxy)ethyl polystyrene;
  2-(3,5-dimethoxy-4-formylphenoxy)ethoxy-methyl polystyrene;
  2-(3,5-dimethoxy-4-formylphenoxy)ethoxy polystyrene;
  (3-Formylindolyl)acetamidomethyl polystyrene;
  (4-Formyl-3-methoxyphenoxy) grafted (polyethyleneglycol)-polystyrene; or
  (4-Formyl-3-methoxyphenoxy)methylpolystyrene.

Abbreviations used in the Examples are as follows:
APCI=atmospheric pressure chemical ionization
BOC=tert-butoxycarbonyl
BOP=(1-benzotriazolyloxy)tris(dimethylamino)phosphonium hexafluorophosphate
d=day
DIAD=diisopropyl azodicarboxylate
DCC=dicyclohexylcarbodiimide
DCE=dichloroethane
DCM=dichloromethane
DIC=diisopropylcarbodiimide
DIEA=diisopropylethylamine
DMA=N,N-dimethylacetamide
DMAP=dimethylaminopyridine
DME=1,2 dimethoxyethane
DMF=N,N-dimethylformamide
DMPU=1,3-dimethypropylene urea
DMSO=dimethylsulfoxide
EDC=1-ethyl-3-(3-dimethylaminopropyl)-carbodiimide hydrochloride
EDTA=ethylenediamine tetraacetic acid
ELISA=enzyme—linked immunosorbent assay
ESI=electrospray ionization
ether=diethyl ether
EtOAc=ethyl acetate
FBS=fetal bovine serum
g=gram
h=hour
HBTU=O-benzotriazol-1-yl-N,N,N',N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole
mp=melting point
MS=mass spectrometry
N=normal
NMM=N-methylmorpholine, 4-methylmorpholine
NMR=nuclear magnetic resonance spectroscopy
p.o.=per oral
PBS=phosphate buffered saline solution
PMA=phorbol myristate acetate
ppm=parts per million psi=pounds per square inch
$R_f$=relative TLC mobility
rt=room temperature
s.c.=subcutaneous
SPA=scintillation proximity assay
TEA=triethylamine
TFA=trifluoroacetic acid
THF=tetrahydrofuran
THP=tetrahydropyranyl
TLC=thin layer chromatography
TMSBr=bromotrimethylsilane, trimethylsilylbromide
$T_r$=retention time Thus, in an embodiment, the following compounds may be synthesized using the following procedures and according to the Schemes I through IX described herein.

Procedure A:

To a solution of a carboxylic acid (1.0 mmol) in DMF (6 mL) was added an amino acid methyl ester (1.0 mmol), DIC (3.0 mmol), HOBt (3.0 mmol) and DMAP (catalyst) and the mixture was stirred overnight. Alternatively, to a solution of a carboxylic acid (1.0-1.5 mmol) in DMF (6 mL) was added an amino acid methyl ester (1.0-1.5 mmol), HBTU (1.0-1.5 mmol), and DIEA (2.0-3.0 mmol) and the mixture was stirred overnight. After completion of the reaction, sufficient amount of water was added and the mixture was extracted with ethyl acetate (3×15 ml). The combined organic layer was washed with 5% citric acid solution, saturated sodium bicarbonate solution and brine, and then dried over sodium sulfate. Alternatively, the combined organic layer was washed with 1N HCl, saturated sodium bicarbonate solution and brine, and then dried over sodium sulfate. The solvent was removed in vacuum to afford the amide, which was used for further transformation without further purification.

Procedure B:

To a mixture of phenol and the aryl fluoride (2 eq) in DMF was added solid potassium carbonate (10 eq), and the mixture was heated at 80° C. for 12 h. After completion of the reaction, sufficient amount of water was added, and the mixture was extracted with ethyl acetate. The combined organic layer was washed with water and brine, dried over sodium sulfate. The solvent was removed in vacuum and the crude material obtained was purified by flash chromatography to afford the desired aryl ethers.

Procedure C:

To a solution of ester in THF, $CH_3OH$ (5:1), 2N-lithium hydroxide solution (5 eq) was added, and the resulting reaction mixture was stirred at 0° C. to rt for 1.5 h. Alternatively, to a solution of ester in THF, $H_2O$ (4:1), lithium hydroxide (10 eq) was added, and the resulting reaction mixture was heated at 50° C. for 12 h. After completion of the reaction, 1N HCl was used to neutralize the base, and then the solvents were removed under vacuum. The product was extracted with ethyl acetate, the organic layer was washed with brine, dried over sodium sulfate, and the solvent was removed in vacuum to afford the product carboxylic acid in pure form.

Procedure D:

To a solution of phenyl bromide in DME or toluene were added corresponding boronic acid (2-3 eq), Pd $(PPh_3)_4$ (0.2-0.3 eq), 2N $Na_2CO_3$ solution (2.5 eq). The mixture was heated at 75° C. for 12 h. After completion of the reaction, solvent was evaporated in vacuo. During the reaction, some of the ester was hydrolyzed to the corresponding acid. Therefore, if desired, crude product so obtained was re-esterfied by dissolving it in $CH_3OH$ containing 1% of HCl. The mixture was refluxed for 6 h and after the completion of the reaction, the mixture was concentrated under reduced pressure. The residue was purified by flash chromatography to afford the desired ester. The resulting ester was hydrolyzed as described in procedure C yielding the pure acid.

Procedure E:

To a solution of phenyl bromide carboxylic acid in DME or toluene were added corresponding boronic acid (2-3 eq), Pd $(PPh_3)_4$ (0.2-0.3 eq), 2N $Na_2CO_3$ solution (2.5 eq). The mixture was heated at 75° C. for 12 h. After completion of the reaction, the mixture was filtered and ethyl acetate (with 5% THF) and excess 1N HCl was added. The organic layer was then washed with 1N HCl and brine, dried over sodium sulfate, and the solvent was removed in vacuum. The residue was purified by trituration or flash chromatography to afford the desired acid.

Procedure F:

To a solution of an aniline (1.0 mmol) in DCM (10 mL) was added a sulfonyl chloride or, alternatively, an acid chloride (1.0 mmol), and pyridine (10.0 mmol) and the mixture was stirred overnight. After completion of the reaction, 50 mL of DCM was added and the organic layer was washed with 1N HCl, saturated sodium bicarbonate solution and brine, and then dried over sodium sulfate. The solvent was removed in vacuum to afford the corresponding sulfonamide or amide, which was purified by flash chromatography.

Procedure G:

To a solution of an aniline (1.0 mmol) in DCE (10 mL) was added an aldehyde (2.0-2.2 mmol), acetic acid (3.0 mmol) and sodium triacetoxyborohydride (2.5 mmol) and the mixture was stirred overnight. After completion of the reaction, 50 mL of DCM was added and the organic layer was washed with 1N HCl, saturated sodium bicarbonate solution and brine, and then dried over sodium sulfate. The solvent was removed in vacuum to afford the amine, which was purified by flash chromatography.

Procedure H:

To a solution of a phenol (1.0 mmol) in DMF (5 mL) was added an alkyl halide (1.2 mmol) and potassium carbonate (2.5 mmol). Note that a catalytic amount of sodium iodide is added when an alkyl chloride is employed in the reaction. After completion of the reaction, 5 mL of ethyl acetate and 5 mL of water was added. The organic layer was washed with water and then dried over sodium sulfate. The solvent was removed in vacuum to afford the ether, which was purified by flash chromatography.

Procedure I:

To a solution of a salicylic acid (1.0 mmol) in DMF (2 mL) was added an alkyl bromide (2.0-2.5 mmol), and potassium carbonate (2.0-2.5 mmol) and the mixture was heated at 100° C. for 1 h. After completion of the reaction, 12 mL of ether and 10 mL of brine was added and the organic layer was washed with brine, and then dried over magesium sulfate. The solvent was removed in vacuum to afford the product, which was purified by flash chromatography.

Procedure J:

To 0.1 mmol of Wang resin bound product was added 2 ml of 20% TFA in DCM. The reaction was agitated for 30-120 minutes. The cleaved product was collected and the solvent was removed in vacuum to afford the compound, which was purified by flash chromatography.

Procedure K:

To a resin bound phenyl bromide suspended in DME or toluene were added corresponding boronic acid (1-4 eq), Pd(PPh$_3$)$_4$ (0.1-0.2% eq), 2N Na$_2$CO$_3$ solution (2.5 eq). The mixture was heated at 75° C. for 12 h. Upon completion of the reaction, the resin was washed DMF (3×), MeOH (3×), and DCM (3×).

Procedure L:

To a resin bound amine (1.0 mmol) suspended in DMF (20 mL) was added a carboxylic acid (1.0-3.0 mmol), DIC (1.0-3.0 mmol), HOBt (1.0-3.0 mmol) and DMAP (catalyst) and the mixture was stirred overnight. Conversely, to a resin bound carboxylic acid (1.0 mmol) suspended in DMF (20 mL) was added an amine (1.0-3.0 mmol), DIC (1.0-3.0 mmol), HOBt (1.0-3.0 mmol) and DMAP (catalyst) and the mixture was stirred overnight. Upon completion of the reaction, the resin was washed DMF (3×), MeOH (3×), and DCM (3×).

Procedure M:

To a resin bound amine (1.0 mmol) suspended in DCE (20 mL) was added an aldehyde (5.0 mmol), acetic acid (5.0 mmol) and sodium cyanoborohydride (10.0 mmol) and the mixture was stirred overnight. Upon completion of the reaction, the resin was washed DMF (3×), MeOH (3×), and DCM (3×).

Procedure N:

To a resin bound amine (1.0 mmol) suspended in DCM (20 mL) was added a sulfonyl chloride or, alternatively, an acid chloride (3.0-5.0 mmol), and pyridine (5.0-10.0 mmol) and the mixture was stirred overnight. Upon completion of the reaction, the resin was washed DMF (3×), MeOH (3×), and DCM (3×).

Example 1

3-biphenyl-4-yl-2-[5-bromo-2-(4-tert-butyl-benzenesulfonylamino)-benzoylamino]-propionic acid (2S)-(2-amino-5-bromo-benzoyl-amino)-3-biphenyl-4-yl-propionic acid methyl ester (1.53 g, 80%) was prepared from (2S)-amino-3-biphenyl-4-yl-propionic acid methyl ester (1.0 g, 4.1 mmol) and 5-bromo-2-amino-benzoic acid (1.23 g, 4.9 mmol) as described in procedure A.

To a stirring solution of (2S)-(2-amino-5-bromo-benzoyl-amino)-3-biphenyl-4-yl-propionic acid methyl ester (1.0 g, 2 mmol) prepared above dissolved in DCM containing pyridine (1.58 g, 4 mmol), was added 4-tert-butylbenzenesulfonyl chloride (1.20 g, 2.5 mmol) at 0° C. The reaction mixture was stirred at rt for 3 h, extracted with DCM, washed with 1M HCl and brine, and was concentrated in vacuo, followed by column chromatography purification (silica, CH$_2$Cl$_2$) giving 3-biphenyl-4-yl-2-[5-bromo-2-(4-tert-butyl-benzenesulfonylamino)-benzoylamino]-propionic acid methyl ester (1.25 g) as a white solid which was hydrolyzed according to Procedure C yielding the title compound (1.23 g) as a white solid.

$^1$H-NMR(400 MHz, CD$_3$COCD$_3$): 3.38 (dd, 1H), 3.47 (dd, 1H), 5.09 (m, 1H), 7.32 (m, 1H), 7.42 (m, 4H), 7.60 (m, 4H), 7.82 (m, 1H), 7.89 (m, 1H), 8.17 (m, 1H), 8.23 (m, 1H), 8.58 (s, 1H), 8.76 (m, 1H), 9.30 (d, 1H); LC/MS (m/z): 397(M+1)$^+$.

Example 2

(2S)-[(3'-Chloro-4'-fluoro4-hydroxy-biphenyl-3-carbonyl)-amino]-3-(3'-trifluoromethyl-biphenyl4-yl)-propionic acid To 40 g (200 mmol) of 5-bromo-2-hydroxy-benzoic acid methyl ester, and 11.0 g (220 mmol) of sodium methoxide in 500 mL of anhydrous DMA was added 13.30 g (71 mmol) of Merrifield resin. The mixture was heated at 110° C. overnight. The resin was washed with H$_2$O, DMF, MeOH, DCM (three times of each), and dried.

The resin-bound 3'-chloro-4'-fluoro-4-hydroxy-biphenyl-3-carboxylic acid methyl ester was prepared with 1.0 g (3.0 mmol) of above resin-bound 5-bromo-2-hydroxy-benzoic acid methyl ester and 1.6 g (9.0 mmol) of 3-chloro-4-fluoro-phenylboronic acid as described in Procedure K. The resulting resin-bound methyl benzoate was hydrolyzed with LiOH/H$_2$O/THF/ethanol at rt for 3 days.

The resin-bound 3-(4-bromo-phenyl)-(2S)-2-[(3'-chloro-4'-fluoro-4-hydroxy-biphenyl-3-carbonyl)-amino]-propionic acid methyl ester (1.0 g, 3.0 mmol) was obtained by following Procedure L with the resin-bound 3'-chloro-4'-fluoro-4-hydroxy-biphenyl-3-carboxylic acid (1.0 g, 3.0 mmol) and 2-L-amino-3-(4-bromo-phenyl)-propionic acid methyl ester-hydrochloride (2.6 g, 9.0 mmol).

The resin-bound 3-(4-bromo-phenyl)-(2S)-2-[(3'-chloro-4'-fluoro -4-hydroxy-biphenyl-3-carbonyl)-amino]-propionic acid methyl ester (100 mg, 0.3 mmol) was reacted with 3-trifluoromethyl-phenylboronic acid (285 mg, 1.5 mmol) by following Procedure K. The resulting resin-bound methyl ester was hydrolyzed with LiOH/H$_2$O/THF/methanol, and washed with DMF, MeOH, DCM (three times of each). The title compound was then cleaved from the resin with TMSBr/TFA/DCM (1:1:5) at rt for 4 h. The residue obtained after removing the solvent was purified by column chromatography to give 75 mg of the title compound.

$^1$H-NMR(400 MHz, CDCl$_3$): 3.38 (m, 2H), 5.15 (m, 1H), 6.80 (d, 1H), 7.10 (m, 2H), 7.28 (m, 1H), 7.33 (m, 3H), 7.46 (dd, 1H), 7.52-7.61 (m, 5H), 7.71 (d, 1H), 7.79 (s, 1H); LC/MS (m/z): 558 (M+1)$^+$.

Example 3

(2S)-[2-(biphenyl-4-ylmethoxy)-benzoylamino]-3-[4-(biphenyl4-ylmethoxy)-phenyl]-propionic acid (S)-3-(4-benzyloxy-phenyl)-2-(5-bromo-2-hydroxy-benzoylamino)-propionic acid methyl ester (2.70 g) was prepared from S-2-amino-3-(4-benzyloxy-phenyl)-propionic acid methyl ester-hydrochloride (5.54 g, 17.2 mmol), 5-bromo-2-hydroxy-benzoic acid (3.7 g, 17.2 mmol) as described in Procedure A, except for an adapted work-up. After reaction completion, the reaction mixture was poured onto 150 mL of 1N HCl and 150 mL of EtOAc. The organic layer was washed with 1N HCl, saturated sodium bicarbonate, dried over sodium sulfate and evaporated. The crude material was purified over silica gel (8:2, DCM-hexanes).

(S)-3-(4-benzyloxy-phenyl)-2-(5-bromo-2-hydroxy-benzoylamino)-propionic acid methyl ester (750 mg, 1.5 mmol) was dissolved in 30 mL of MeOH, 100 mg of 10% Pd/C added, and the mixture stirred for 2.5 h under 40 psi of H$_2$. The mixture was filtered and solvent evaporated. The resulting residue was dissolved in DCM, washed with saturated NaHCO$_3$, dried over sodium sulfate and evaporated to give (S)-2-(2-hydroxy-benzoylamino)-3-(4-hydroxy-phenyl)-propionic acid methyl ester (409 mg).

(S)-2-[2-(biphenyl4-ylmethoxy)-benzoylamino]-3-[4-(biphenyl-4-ylmethoxy)-phenyl]-propionic acid methyl ester (48 mg) was prepared from (S)-2-(2-hydroxy-benzoylamino)-3-(4-hydroxy-phenyl)-propionic acid methyl ester (175 mg, 0.55 mmol) and 4-biphenylmethyl chloride (240 mg, 1.2 mmol) with $K_2CO_3$ (306 mg, 2.2 mmol) as described in Procedure H and purified over silica gel (8:2, DCM-hexanes).

(S)-2-[2-(biphenyl-4-ylmethoxy)-benzoylamino]-3-[4-(biphenyl-4-ylmethoxy)-phenyl]-propionic acid methyl ester (50 mg, 0.077 mmol) was dissolved in 5 mL of THF-MeOH (4-1), cooled to 0° C. and 1.1 equiv of 2 N LiOH added. After 30 minutes, 3.2 additional equiv of 2N LiOH was added and the reaction stirred for 30 minutes. The reaction was worked up according to Procedure C to give 29 mg of the title compound.

$^1$H-NMR(400 MHz, DMSO-$d_6$): 2.90 (m, 1H), 3.19 (m, 1H), 4.90 (m, 3H), 5.10 (m, 2H), 6.80 (d, 2H), 6.92 (d, 2H), 6.98 (m, 1H), 7.09 (m, 1H), 7.45-7.29 (m, 11 H ), 7.57-7.51 (m, 8H), 8.24 (m, 1H), 8.53 (d, 1H); LC/MS (m/z): 634.1 (M+1)$^+$.

Example 4

(2S)-3-[4-(4-tert-butyl-benzyloxy)-phenyl]-2-{5-chloro-2-[(naphthalen-1-ylmethyl)-amino]-benzoylamino}-propionic acid (S)-2-Tert-butoxycarbonylamino-3-[4-(4-tert-butyl-benzyloxy)-phenyl]-propionic acid methyl ester (290 mg) was prepared from (S)-2-tert-butoxycarbonylamino-3-(4-hydroxy-phenyl)-propionic acid methyl ester (425 mg, 1.4 mmol) and 4-tert-butylbenzyl bromide (1.6 mmol) with $K_2CO_3$ (398 mg, 2.9 mmol) as described in Procedure H and purified over silica gel (8:2, DCM-hexanes).

(S)-2-Tert-butoxycarbonylamino-3-[4-(4-tert-butyl-benzyloxy)-phenyl]-propionic acid methyl ester (290 mg, 0.66 mmol) was treated with 4 mL of 4N HCl in dioxane for 1 h at room temperature. The solvent was evaporated and the remaining solid triturated with diethyl ether to give (S)-2-amino-3-[4-(4-tert-butyl-benzyloxy)-phenyl]-propionic acid methyl ester-hydrochloride (214 mg).

(S)-2-(Amino-5-chloro-benzoylamino)-3-[4-(4-tert-butyl-benzyloxy)-phenyl]-propionic acid methyl ester (175 mg) was prepared from (S)-2-amino-3-[4-(4-tert-butyl-benzyloxy)-phenyl]-propionic acid methyl ester-hydrochloride (214 mg, 0.57 mmol) and 2-amino-5-chloro-benzoic acid (101 mg) as described in Procedure A, except for an adapted work-up. After reaction completion, the reaction mixture was poured onto 5 mL of 1N HCl and 5 mL of EtOAc. The organic layer was washed with 1N HCl, saturated sodium bicarbonate, dried over sodium sulfate and evaporated. The crude material was purified over silica gel (DCM).

(S)-3-[4-(4-tert-butyl-benzyloxy)-phenyl]-2-{5-chloro-2-[(naphthalen-1-ylmethyl)-amino]-benzoylamino}-propionic acid methyl ester (140 mg) was prepared from (S)-2-(2-amino-5-chloro-benzoylamino)-3-[4-(4-tert-butyl-benzyloxy)-phenyl]-propionic acid methyl ester (174 mg, 0.35 mmol) and 1-naphthaldehyde (0.106 mL, 0.77 mmol) according to Procedure G, except for the addition of 1 equiv. of $NaBH(OAc)_3$ after 4 h and an adapted work-up. After reaction completion, 5 mL of DCM and 10 mL of saturated sodium bicarbonate were added and the organic layer dried over sodium sulfate and evaporated. The crude material was purified over silica gel (6:4, DCM-hexanes).

(S)-3-[4-(4-tert-butyl-benzyloxy)-phenyl]-2-{5-chloro-2-[(naphthalen-1-ylmethyl)-amino]-benzoylamino}-propioinic acid methyl ester (120 mg, 0.19 mmol) was dissolved in 5 mL of THF-MeOH (4-1), cooled to 0° C. and 1.1 equiv of 2 N LiOH added. After 30 minutes, 3.2 additional equiv of 2N LiOH was added and the reaction stirred for 60 minutes. The reaction was worked up according to Procedure C to give 90 mg of the title compound.

$^1$H-NMR(400 MHz, DMSO-$d_6$): 1.26 (s, 9H), 2.97 (m, 1H), 3.10 (m, 1H), 4.48 (m, 1H), 4.80 (m, 2H), 4.98 (s, 2H), 6.69 (d,1H), 6.90 (d, 2H), 7.20 (d, 2H), 7.27 (m, 1H), 7.46-7.31 (m, 6H), 7.55 (m, 2H), 7.66 (m, 1H), 7.84 (d, 1H), 7.95 (m, 1H),8.05-8.12 (m, 2H), 8.71 (d, 1H); LC/MS (m/z): 621.2 (M+1)$^+$.

Example 5

(2S)-{5-chloro-2-[(naphthalen-1-ylmethyl)-amino]-benzoylamino}-3-(4'-phenoxy-biphenyl-4-yl)-propionic acid (S)-2-(2-amino-5-chloro-benzoylamino)-3-(4-bromophenyl)-propionic acid methyl ester (2.90 g) was prepared from (S)-2-amino-3-(4-bromo-phenyl)-propionic acid methyl ester-hydrochloride (4.0 g, 13.5 mmol) and 5-amino-2-chloro-benzoic acid (2.33 g, 13.5 mmol) as described in Procedure A. The product was purified over silica gel ($CH_2Cl_2$:$CH_3OH$).

(S)-3-(4-Bromo-phenyl)-2-{5-chloro-2-[(naphthalen-1-ylmethyl)-amino]-benzoylamino}-propionic acid methyl ester was prepared from (S)-2-(2-amino-5-chloro-benzoylamino)-3-(4-bromo-phenyl)-propionic acid methyl ester (2.5 g, 6.07 mmol) and 1-naphthaldehyde (2.0 g, 13.3 mmol) according to Procedure G, except for the following: after completion of the reaction, 100 mL of DCM was added and the organic washed with saturated sodium bicarbonate, dried over sodium sulfate, and evaporated. The crude material was purified over silica gel (8:2, DCM-hexanes).

(S)-3-(4-Bromo-phenyl)-2-{5-chloro-2-[(naphthalen-1-ylmethyl)-amino]-benzoylamino}-propionic acid methyl ester (150 mg, 0.36 mmol), Pd (PPh$_3$)$_4$ (84 mg, 0.072 mmol), and 4-phenoxyphenylboronic acid (233 mg, 1.09 mmol) were dissolved in 5 mL of toluene, a 1M $Na_2CO_3$ solution (0.9 mL, 0.91 mmol) added and the mixture heated at 80° C. for 12 h. The reaction mixture was diluted with 5 mL of $CH_2Cl_2$ and filtered, all volatiles are removed under vaccum and the ester product was hydrolyzed according to Procedure C, and purified over silica gel (ethyl acetate:hexanes) to give the title compound(118 mg) as a white solid.

$^1$HNMR (400MHz, DMSO-$d_6$): 3.08 (dd, 1H), 3.20 (dd, 1H), 4.54-4.64 (m, 1H), 4.79(d, 2H), 6.70 (d, 1H), 7.00-7.09 (m, 4H), 7.12-7.20 (m, 1H), 7.26 (dd, 1H), 7.34-7.46 (m, 6H), 7.51-7.60 (m, 4H), 7.62-7.71(m, 3H) 7.80-7.88 (m, 1H), 7.92-7.99 (m, 1H), 8.02-8.14 (m, 2H), 8.79 (d, 1H), 12.80 (s, 1H). LC/MS (m/z): 627.1 (M+1)$^+$.

Example 6

3-Biphenyl-4-yl-(2S)-[2-3,5-bistrifluoromethyl-benzoylamino)-5-bromo-benzoylamino]-propionic acid To a solution of Fmoc-L-biphenylalanine (40.0 mmol) in DMF (40 mL) was added Wang resin (16.0 mmol), HOBt (40.0 mmol) in DMF (40 mL), DIC (40.0 mmol) in DMF (40 mL) and DMAP (0.40 mmol) and the mixture was shaken overnight, according to Procedure L. The reaction mixture was drained and the resin washed with DMF, methanol and DCM (3×150 mL each solvent).

The resulting resin-bound Fmoc-L-biphenylalanine was deprotected with 20% piperidine in DMF (150 mL) for 2 hours. The reaction mixture was drained and washed 3× with DMF, methanol and DCM (3×150 mL each solvent).

To the resin-bound L-biphenylalanine (12 mmol), a solution of 2-amino-5-bromobenzoic acid (30 mmol) in DMF (30 mL), HOBt (30 mmol) in DMF (30 mL) and DIC (30 mmol) in DMF (30 mL) were added and the mixture was shaken overnight, according to Procedure L. The reaction mixture was drained and washed with DMF, methanol and DCM (3×150 mL each solvent).

To the resin-bound (S)-2-(2-amino-5-bromo-benzoylamino)-3-biphenyl-4-yl-propionic acid (0.12 mmol) was added a solution of 3,5-bis-(trifluoromethyl)benzoyl chloride (0.3 mmol) and pyridine (0.3 mmol) and the mixture agitated for 72 hours, according to Procedure N. The reaction mixture was drained and washed with DMF, methanol and DCM (3×5 mL each solvent).

Resin bound (S)-3-biphenyl-4-yl-2-[2-(3,5-bistrifluoromethyl-benzoylamino)-5-bromo-benzoylamino]propionic acid was treated with 20% TFA in DCM (2 mL) for 1 hour, according to Procedure J. The filtrate was collected and evaporated to give (41.2 mg of the title compound.The product was purified via chromatography (silica, DCM/ethyl acetate). LC/MS (m/z): 679, 681 [(M)$^+$, (M+2)$^+$].

Example 7

(2S)-{2-chloro-5-[(naphthalen-1-ylmethyl)-amino]-benzoylamino}-3-(4'-phenoxy-biphenyl-4-yl)-propioinic acid (S)-2-(5-Amino-2-chloro-benzoylamino)-3-(4-bromo-phenyl)-propionic acid methyl ester (316 mg) was prepared from (S)-2-Amino-3-(4-bromo-phenyl)-propionic acid methyl ester-hydrochloride (1.5 g, 5.1 mmol) and 5-amino-2-chloro-benzoic acid (909 mg, 5.1 mmol) as described in Procedure A, except for an adapted work-up. After reaction completion, the reaction mixture was poured onto 100 mL of 1N HCl and 50 mL of EtOAc. The organic layer was washed with 1N HCl, 10% sodium carbonate, dried over sodium sulfate and evaporated. The crude material was purified over silica gel (DCM-EtOAc, 9-1).

(S)-3-(4-Bromo-phenyl)-2-{2-chloro-5-[(naphthalen-1-ylmethyl)-amino]-benzoylamino}-propionic acid methyl ester (264 mg) was prepared from (S)-2-(5-amino-2-chloro-benzoylamino)-3-(4-bromo-phenyl)-propionic acid methyl ester (316 mg, 0.77 mmol) and 1-naphthaldehyde (0.231 mL, 1.7 mmol) according to Procedure G, except for the following: the reaction was done in 15 mL DCE and 2 mL THF, two additional equiv. NaBH(OAc)$_3$ were added after 2 h and an adapted work-up. After reaction completion, 100 mL of DCM was added and the organic washed with saturated sodium bicarbonate, dried over sodium sulfate, and evaporated. The crude material was purified over silica gel (8:2, DCM-hexanes).

(S)-3-(4-Bromo-phenyl)-2-{2-chloro-5-[(naphthalen-1-ylmethyl)-amino]-benzoylamino}-propionic acid methyl ester (264 mg, 0.48 mmol), Pd(PPh$_3$)$_4$ (86 mg, 0.096 mmol), and 4-phenoxyphenylboronic acid (205 mg, 0.96 mmol) were dissolved in 5 mL of toluene, a 1M Na$_2$CO$_3$ solution (1.2 mL, 1.2 mmol) added and the mixture heated at 80° C. for 16 h. The reaction mixture was evaporated to dryness and the crude mixture purified over silica gel (7:3, DCM-hexanes) to give (S)-2-{2-chloro-5-[(naphthalen-1-ylmethyl)-amino]-benzoylamino}-3-(4'-phenoxy-biphenyl-4-yl)-propioinic acid methyl ester (118 mg).

(S)-2-{2-Chloro-5-[(naphthalen-1-ylmethyl)-amino]-benzoylamino}-3-(4'-phenoxy-biphenyl-4-yl)-propioinic acid methyl ester (80 mg, 0.12 mmol) was dissolved in 5 mL of THF-MeOH (4-1), cooled to 0° C. and 1.1 equiv of 2 N LiOH added. After 30 minutes, 3.3 additional equiv of 2N LiOH was added and the reaction stirred for 60 minutes. The reaction was worked up according to Procedure C to give 60 mg of the title compound.

$^1$H-NMR(400 MHz, DMSO-d$_6$): 2.97 (m, 1H), 3.15 (m, 1H), 4.57 (m, 1H), 4.65 (d, 2H), 6.58-6.64 (m, 3H), 6.97 (m, 2H), 7.02-7.09 (m, 3H), 7.17 (m, 1H), 7.34 (d, 2H), 7.39-7.46 (m, 6H), 7.47-7.57 (m, 4H), 7.84 (m, 1H), 7.94 (m, 1H), 8.09 (m, 1H), 8.66 (d, 1H); LC/MS (m/z): 627.1 (M+1)$^+$.

Example 8

(2S)-{4-[(Naphthalen-1-ylmethyl)-amino-benzoylamino}-3-(4'-phenoxy-biphenyl-4-yl)-propionic acid (S)-2-(4-Amino-benzoylamino)-3-(4-bromo-phenyl)-propionic acid methyl ester (415 mg) was prepared from (S)-2-amino-3-(4-bromo-phenyl)-propionic acid methyl ester-hydrochloride (1.5 g, 5.1 mmol) and 4-amino-benzoic acid (698 mg, 5.1 mmol) as described in Procedure A, except for an adapted work-up. After reaction completion, the reaction mixture was poured onto 100 mL of 1N HCl and 100 mL of EtOAc. The organic layer was washed with 1N HCl (2×), 10% sodium carbonate, dried over sodium sulfate and evaporated. The crude material was purified over silica gel (DCM-EtOAc, 9-1).

(S)-3-(4-Bromo-phenyl)-2-{4-[(naphthalen-1-ylmethyl)-amino]-benzoylamino}-propionic acid methyl ester (273 mg) was prepared from (S)-2-(4-amino-benzoylamino)-3-(4-bromo-phenyl)-propionic acid methyl ester (415 mg, 1.1 mmol) and 1-naphthaldehyde (0.331 mL, 2.4 mmol) according to Procedure G, except for the following: the reaction was done in 15 mL DCE and 5 mL THF, was allowed to stir for 15 min before NaBH(OAc)$_3$ was added, was treated with two additional equiv. NaBH(OAc)$_3$ after 2 h, and an adapted work-up. After reaction completion, 100 mL of DCM was added and the organic washed with saturated sodium bicarbonate, dried over sodium sulfate, and evaporated. The crude material was triturated with MeOH.

(S)-3-(4-Bromo-phenyl)-2-{4-[(naphthalen-1-ylmethyl)-amino]-benzoylamino}-propionic acid methyl ester (273 mg, 0.53 mmol), Pd (PPh$_3$)$_4$ (96 mg, 0.11 mmol), and 4-phenoxyphenylboronic acid (226 mg, 1.1 mmol) were dissolved in 5 mL of toluene, a 1M Na$_2$CO$_3$ solution (1.3 mL, 1.3 mmol) added and the mixture heated at 80° C. for 16 h. The reaction mixture was evaporated to dryness and the crude mixture purified over silica gel (8:2, DCM-hexanes) to give (S)-2-{4-[(naphthalen-1-ylmethyl)-amino]-benzoylamino}-3-(4'-phenoxy-biphenyl-4-yl)-propionic acid methyl ester (107 mg).

(S)-2-{4-[(naphthalen-1-ylmethyl)-amino]-benzoylamino}-3-(4'-phenoxy-biphenyl-4-yl)-propionic acid methyl ester (80 mg, 0.13 mmol) was dissolved in 5 mL of THF-MeOH (4-1), cooled to 0° C. and 1.1 equiv of 2 N LiOH added. After 30 minutes, 3.3 additional equiv of 2N LiOH was added and the reaction stirred for 60 minutes. The reaction was worked up according to Procedure C to give 53 mg of the title compound. $^1$H-NMR(400 MHz, DMSO-$d_6$): 3.08 (m, 1H), 3.17 (m, 1H), 4.59 (m, 1H), 4.76 (d, 2H), 6.63 (d, 2H), 6.84 (m, 1H), 7.02-7.07 (m, 4H), 7.18 (m, 1H), 7.36-7.49 (m, 6H), 7.53-7.65 (m, 8H), 7.84 (d, 1H), 7.95, (m, 1H), 8.12, (m, 1H), 8.26 (d, 1H);LC/MS (m/z): 593.1 (M+1)$^+$.

Example 9

6-{(2S)-[1-carboxy-2-(4'-phenoxy-biphenyl-4-yl)-ethylcarbamoyl]-4-chloro-phenylamino}-hexanoic acid (S)-2-Amino-3-(4'-phenoxy-biphenyl-4-yl)propionic acid methyl ester was prepared following Procedure D using (S)-4-bromo-phenyl alanine (7.32 g, 30 mmol), 4-phenoxy-benzene boronic acid (12.84 g, 60 mmol), palladium tetrakis-triphenylphosphine (3.47 g, 3 mmol) and Na$_2$CO$_3$(aq) (2.0 N, 75 mL, 150 mmol) in DME (180 mL). The mixture was heated at 93° C. for 24 h. After completion of the reaction, 4 N HCl in dioxane solution was added to neutralize the reaction mixture. The solvents were evaporated. The solid residue was washed with ether and methanol to remove some impurities, and then refluxed with 4 N HCl in dioxane solution (15 mL) and methanol (120 mL) for 6 h to form methyl ester. The solvents were evaporated. The residue was partitioned between ethyl acetate (100 mL) and saturated NaHCO$_3$ (aq) solution (100 mL). The aqueous layer was separated and extracted again with ethyl acetate (4×100 mL). The combined organic extracts were dried over Na$_2$SO$_4$. Evaporation of the solvent in vacuum gave the product as yellow solid (8.84 g, 25.4 mmol).

(S)-2-(2-amino-5-chloro-benzoylamino)-3-(4'-phenoxy-biphenyl-4-yl)-propionic acid methyl ester was prepared following Procedure A using 2-amino-5-chloro-benzoic acid (1.23 g, 7 mmol), (S)-2-amino-3-(4'-phenoxy-biphenyl-4-yl) propionic acid methyl ester (2.43 g, 7 mmol), HBTU (3.19 g, 8.4 mmol) and DIEA (2.46 mL, 14 mmol) in DMF (35 mL). Purification by flash chromatography (ethyl acetate/hexanes 1:3, 1:2) gave the title compound as yellow solid (3.25 g, 6.49 mmol,).

(S)-6-{4-Chloro-2-[1-methoxycarbonyl-2-(4'-phenoxy-biphenyl-4-yl)-ethylcarbamoyl]-phenylamino}-hexanoic acid methyl ester was prepared following Procedure G using (S)-2-(2-amino-5-chloro-benzoylamino)-3-(4'-phenoxy-biphenyl-4-yl)propionic acid methyl ester (401 mg, 0.8 mmol), 6-oxo-hexanoic acid methyl ester (231 mg, 1.6 mmol), acetic acid (2.4 mmol), sodium triacetoxyborohydride (437 mg, 97%, 2 mmol) and DCE (6 mL). Purification by flash chromatography (ethyl acetate/hexanes 1:3) gave the title compound as yellow oil (418 mg).

The title compound was prepared following Procedure C using (S)-6-{4-chloro-2-[1-methoxycarbonyl-2-(4'-phenoxy-biphenyl-4-yl)-ethylcarbamoyl]-phenylamino}-hexanoic acid methyl ester (67.6 mg, 0.107 mmol), LiOH(aq) (2.0 N, 0.36 mL, 0.72 mmol), THF (2 mL) and MeOH (0.5 mL). The mixture was stirred at 0° C. for 22 h. The title compound was obtained as white solid (52.9 mg). $^1$H-NMR (400 MHz, DMSO-$d_6$): 8.70 (d, 1H), 7.02-7.65(m, 16H), 6.64(d, 1H), 4.59(ddd, 1H), 2.98-3.21(m, 3H), 2.16(t, 2H), 1.25-1.51(m, 6H); LC-MS m/z: 601 (M+1)$^+$.

Example 10

(2S)-[5-chloro-2-(5-dimethylamino-naphthalene-1-sulfonylamino)-benzoylamino]-3-(2'-phenoxy-biphenyl-4-yl)-propionic acid (2S)-amino-3-(2'-phenoxy-biphenyl4-yl)propionic acid methyl ester was prepared by following Procedure D using (S)-4-bromo-phenyl alanine (7.32 g, 30 mmol), 2-phenoxy-benzene boronic acid (12.84 g, 60 mmol), palladium tetrakis-triphenylphosphine (3.47 g, 3 mmol) and Na$_2$CO$_3$(aq) (2.0 N, 75 mL, 150 mmol) in DME (180 mL). The mixture was heated at 90° C. for 16 h. After completion of the reaction, 4 N HCl in dioxane solution was added to neutralize the reaction mixture. The solvents were evaporated. The solid residue was washed with ether to remove some impurities, and then refluxed with 4 N HCl in dioxane solution (15 mL) and methanol (120 mL) for 6 h to form methyl ester-hydrochloride salt.

(2S)-(2-amino-5-chloro-benzoylamino)-3-(2'-phenoxy-biphenyl4-yl)-propionic acid methyl ester (1.53 g) was prepared from (S2)-amino-3-(2'-phenoxy-biphenyl-4-yl-propionic acid methyl ester hydrochloride salt (1.8 g, 4.69 mmol) and 5-chloro-2-amino-benzoic acid (0.82 g, 4.69 mmol) as described in Procedure A.

To a stirring solution of (S)-2(2-amino-5-chloro-benzoylamino)-3-(2'-phenoxy-biphenyl-4-yl)propionic acid methyl ester (100 mg, 0.2 mmol) prepared above dissolved in DCM containing pyridine (31.6 mg, 0.4 mmol), was added 5-Dimethylamino-naphthalene-1-sulfonyl chloride (59.1 mg, 0.0.22 mmol) at 0° C. The reaction mixture was stirred at rt for 3 h, extracted with DCM, washed with 1M HCl and brine evaporation followed by column chromatography purification (silica, CH$_2$Cl$_2$) giving (2S)-[5-chloro-2-(5-dimethylamino-naphthalene-1-sulfonylamino)-benzoylamino]-3-(2'-phenoxy-biphenyl-4-yl)-propionic acid methyl ester (100 mg) as a light yellow solid which was hydrolyzed according to Procedure C yielding the title compound (93 mg) as a light yellow solid. LC/MS (m/z): 720 (M+1)$^+$.

Example 11

(2S)-[5-chloro-2-(2-methyl-pentylamino)-benzoylamino]-3-(2'-phenoxy-biphenyl-4-yl)-propionic acid (2S)-[5-chloro-2-(2-methyl-pentylamino)-benzoylamino]-3-(2'-phenoxy-biphenyl-4-yl)-propionic acid methyl ester was prepared following procedure G using (2S)-(2-amino-5-chloro-benzoylamino)-3-(2'-phenoxy-biphenyl-4-yl)-propionicacid methyl ester (100 mg, 0.2 mmol) prepared in Example 10, 2-methyl-pentanal (30 mg, 0.25 mmol) in DCE (4 mL). Purification by flash chromatography (ethyl acetate/hexanes 1:3) gave the title compound as a thick liquid, which was hydrolyzed according to Procedure C yielding the title compound (85 mg). LC/MS (m/z): 571 (M+1)$^+$.

Example 12

(2S)-[2-(biphenyl-4-sulfonylamino)-5-chloro-benzoylamino]-3-(2'-phenoxy-biphenyl-4-yl)-propionic acid (S)-2-Amino-3-(2'-phenoxy-biphenyl-4-yl)propionic acid methyl ester was prepared by following Procedure D using (S)-4-bromo-phenyl alanine (7.32 g, 30 mmol), 2-phenoxy-benzene boronic acid (12.84 g, 60 mmol), palladium tetrakis-triphenylphosphine (3.47 g, 3 mmol) and Na$_2$CO$_3$(aq) (2.0 N, 75 mL, 150 mmol) in DME (180 mL). The mixture was heated at 90° C. for 16 h. After completion of the reaction, 4 N HCl in dioxane solution was added to neutralize the reaction mixture. The solvents were evaporated. The solid residue was washed with ether to remove some impurities, and then refluxed with 4 N HCl in dioxane solution (15 mL) and methanol (120 mL) for 6 h to form methyl ester-hydrochloride salt.

(S)-(2-amino-5-chloro-benzoylamino)-3-(2'-phenoxy-biphenyl-4-yl)-propionic acid methyl ester (1.53 g) was prepared from (S)-2-amino-3-(2'-phenoxy-biphenyl-4-yl-propionic acid methyl ester hydrochloride salt (1.8 g, 4.69 mmol) and 5-chloro-2-amino-benzoic acid (0.82 g, 4.69 mmol) as described in Procedure A.

To a stirring solution of (S)-2(2-amino-5-chloro-benzoylamino)-3-(2'-phenoxy-biphenyl-4-yl) propionic acid methyl ester (60 mg, 0.12 mmol) prepared above dissolved in DCM containing pyridine (19 mg, 0.24 mmol), was added tert-butyl-sulfonyl chloride (42 mg, 0.15 mmol) at 0° C. The reaction mixture was stirred at rt for 3 h, extracted with DCM, washed with 1M HCl and brine evaporation followed by column chromatography purification (silica, $CH_2Cl_2$) giving 2-[2-(Biphenyl-4-sulfonylamino)-5-chloro-benzoylamino]-3-(2'-phenoxy-biphenyl-4-yl) propionic acid methyl ester (77 mg) as a white solid which was hydrolyzed according to Procedure C yielding the title compound (71 mg) as a white solid.

$^1$HNMR (400MHz, DMSO-$d_6$): 3.02(dd, 1H), 3.20(dd, 1H), 4.54-4.64 (m, 1H), 6.83 (d, 2H), 6.93-7.10 (m, 2H), 7.19-7.49 (m, 12H), 7.57 (s, 2H), 7.61-7.67 (m, 2H), 7.70 (s, 1H), 7.79 (s, 4H), 9.28 (d, 1H), 11.35 (s, 1H). LC/MS (m/z): 702.8 (M+1)$^+$.

Example 13

3-(2'-benzyloxy-biphenyl-4-yl)-(2S)-[5-chloro-2-(2-methyl-butylamino)-benzoylamino]-propionic acid 5-chloro-2-(2-methyl-butylamino)-benzoic acid was prepared from 2-amino-5-chloro-benzoic acid (23.31 mmol, 4.0 g) and 2-methylbutyraldehyde (23.31 mmol, 2.0 g) with sodium triacetoxyborohydride (96.62 mmol, 9.88 g) as per Procedure G (5.0 g).

As per Procedure A, 5-chloro-2-(2-methyl-butylamino)-benzoic acid (12.44 mmol, 3 g) was treated with (2S)-amino-3-(4-bromo-phenyl)-propionic acid methyl ester hydrochloride (12.44 mmol, 3.66 g), HBTU (14.92 mmol, 5.66 g) and diisopropylethylamine (37.32 mmol, 4.82 g) to yield 3-(4-bromo-phenyl)-(2S)-[5-chloro-2-(2-methyl-butylamino)-benzoylamino]-propionic acid methyl ester. (4.4 g, 75% yield). LC-MS m/z: 482.8 (M+1)$^+$.

The methyl ester of the title compound was prepared by coupling of the 3-(4-bromo-phenyl)-(2S)-[5-chloro-2-(2-methyl-butylamino)-benzoylamino]-propionic acid methyl ester (1.24 mmol, 0.600 g) and 2-benzyloxyphenyl boronic acid (2.48 mmol, 0.567 g) with Pd (PPh$_3$)$_4$ (0.124 mmol, 0.143 g) as catalyst and Na$_2$CO$_3$ (3.732 mmol) as per Procedure D. The resulting 3-(2'-Benzyloxy-biphenyl-4-yl)-2-[5-chloro-2-(2-methyl-butylamino)-benzoylamino]-propionic acid methyl ester (0.430 g) was then hydrolyzed as per Procedure C to yield the title compound (0.400 g).

$^1$H-NMR (400 MHz, CDCl$_3$): 1.25 (t, 3H), 1.29 (d, 3H), 1.57 (m, 3H), 1.8 (m, 2H), 2.0 (m, 1H), 3.3 (m, 2H), 3.64 (dddd, 2H), 5.38 (m, 3H), 6.76 (d,1H), 6.92 (d, 1H), 7.34 (m, 2H), 7.5-7.61 (m, 8H), 7.67 (d, 2H), 7.88 (d, 2H); LC-MS m/z. 571.3 (M+1)$^+$.

Example 14

6-((3,5-bis-trifluoromethyl-benzoyl)-{(2S)-[1-carboxy-2-(2'-phenoxy-biphenyl-4-yl)-ethylcarbamoyl]-4-chloro-phenylamino}-hexanoic acid (2S)-amino-3-(2'-phenoxy-biphenyl-4-yl)-propionic acid methyl ester was prepared according to Procedure D using (L)-4-bromophenylalanine (8.55 g, 35.0 mmol), 2-phenoxyphenyl boronic acid (10.0 g, 46.7 mmol), Pd (PPh$_3$)$_4$(4.0 g,10% mmol) and 2N Na$_2$CO$_3$ (70 ml, 140 mmol) in 140 mL of DME. After removal of the solvents, the solid was washed with ether to afford the HCl salt of the title compound (10.0 g, 26.2 mmol).

(2S)-amino-3-(2'-phenoxy-biphenyl-4-yl-propionic acid methyl ester (192 mg, 0.5 mmol), was reacted with 5-bromoanthranilic acid (90 mg, 0.5 mmol) as described in Procedure A. The resulting crude compound was alkylated by adipic semialdehyde methyl ester (86 mg, 1.0 mmol) as described in Procedure F. The resulting aniline was next reacted with 3,5-bis(trifluoromethyl)benzoyl chloride (210 mg, 0.75 mmol) as described in Procedure F. The resulting methyl ester was hydrolyzed according to Procedure C to afford the title product (200 mg) as a pure white solid.

$^1$H-NMR(400 MHz, CDCl$_3$): 1.48-1.40 (m, 2H), 1.67-1.62 (m, 4H), 2.36 (t, 2H), 3.10 (t, 2H), 3.18 (dd, 1H), 3.28 (dd, 1H), 4.73 (broad, 1H), 6.30 (d, 1H), 6.56 (d, 1H), 6.90 (d, 2H), 7.01-6.96 (m, 2H), 7.12 (d, 1H), 7.32-7.19 (m, 10H), 7.45 (dd, 1H), 7.52 (d, 2H). LC/MS (m/z): (M+1)$^+$ Example 15

(2S)-2-[((3,5-bis-trifluoromethyl-benzoyl)-pentyl-amino]-5-chloro-benzoylamino]-3-(2'-phenoxy-biphenyl-4-yl)-propionic acid (2S)-amino-3-(2'-phenoxy-biphenyl-4-yl)-propionic acid methyl ester was prepared according to Procedure D using (L)-4-bromophenylalanine (8.55 g, 35.0 mmol), 2-phenoxyphenyl boronic acid (10.0 g, 46.7 mmol), Pd (PPh$_3$)$_4$(4.0 g, 10% mmol) and 2N Na$_2$CO$_3$ (70 ml, 140 mmol) in 140 mL of DME. After removal of the solvents, the solid was washed with ether to afford the HCl salt (10.0 g, 26.2 mmol).

(2S)-amino-3-(2'-phenoxy-biphenyl-4-yl-propionic acid methyl ester (192 mg, 0.5 mmol), was reacted with 5-bromoanthranilic acid (90 mg, 0.5 mmol) as described in Procedure A. The resulting crude intermediate was alkylated by valeraldehyde (86 mg, 1.0 mmol) as described in Procedure F. The resulting aniline was next reacted with 3,5-bis(trifluoromethyl)benzoyl chloride (210 mg, 0.75 mmol) as described in Procedure F. The resulting methyl ester was hydrolyzed according to Procedure C to afford the title compound (200 mg) as a pure white solid.

$^1$H-NMR(400 MHz, CDCl$_3$): 0.86 (t, 3H), 3.71-2.91 (m, 8H), 4.29-4.23 (m, 1H), 4.85 (broad, 1H), 5.09-4.99 (m, 1H), 6.91-6.87 (m, 2H), 7.03-6.96 (m, 2H), 7.30-7.15 (m, 8H), 7.59-7.35 (m, 4H), 8.11-7.91 (m, 2H), 8.52 (s, 1H). LC/MS (m/z): 797(M+1)$^+$.

Biological Assays

The following assay methods may be used to identify compounds of Formula (I) that are effective in binding to and activating an erythropoietin receptor. Compounds of Formula (I) effective in binding to and activating an erythropoietin receptor may be useful in inducing red blood cell production in a subject.

Assay Procedures

EPO-R Indirect Binding Assay 96-well Costar high binding plates (Corning Incorporated, Corning, N.Y. 14831, USA) were coated with 100 μl per well of 5 μg/ml anti-human IgG (Fc specific) antibody (Sigma, Saint Louis, Mo. 63103, USA) at 4° C. overnight and then blocked with 1% BSA-TBST for 1.5 hours at room temperature. Human EPO-R/Fc chimera fusion proteins (R&D Systems, Inc. Minneapolis, Minn. 55413, USA) were then added to each well. The plates were then incubated for 4 hr at 4° C. and washed four times to remove free EPO-R. A 50 μl aliquot of compound working solution and a 50 μl aliquot of $^{125}$I-EPO (Amersham Pharmacia Biotech, Buckinghamshire HP7 9NA, UK) were added to each well and the plate was incubated at 4° C. overnight. The plate was then washed four times with cold 0.5% BSA-TBST and 100 μl of Microscint PS per well was added (Packard, Meriden, Conn. 06450, USA). Bound radioactivity was counted in a TopCount Scintillation Counter (Parkard, Meriden, Conn. 06450, USA). Unlabeled recombinant human EPO (Research Diagnostics, Inc., Flanders, N.J. 07836, USA) was used as competitor to assess nonspecific binding.

EPO-R Direct Binding Assay

A 100 μl per well of 5 μg/ml human EPO-R/Fc chimera fusion proteins was directly coated on the 96-well Costar high binding plates (Corning Incorporated, Corning, N.Y. 14831, USA) at 4° C. overnight and then blocked with 1% BSA-TBST for 1.5 hours at room temperature. A 50 μl aliquot of compound working solution and a 50 μl aliquot of $^{125}$I-EPO (Amersham Pharmacia Biotech, Buckinghamshire HP7 9NA, UK) were added to each well and the plate was incubated at 4° C. overnight. The plate was then washed four times with cold 0.5% BSA-TBST and 100 μl of Microscint PS per well was added (Packard, Meriden, Conn. 06450, USA). Bound radioactivity was counted in a TopCount Scintillation Counter (Parkard, Meriden, Conn. 06450, USA). Unlabeled recombinant human EPO (Research Diagnostics, Inc., Flanders, N.J. 07836, USA) was used as competitor to assess nonspecific binding.

The examples in Table 1 were assayed according to the direct and indirect binding assays described above and in either binding assay the compounds may bind to the EPO receptor with an IC50 of less than 1000 micromolar.

The following assay method may be used to identify compounds of Formula (I) that are effective in stimulating cell proliferation. Compounds of Formula (I) that are effective in stimulating cell proliferation may be useful in inducing red blood cell production in a subject.

Cell Proliferation Assay

UT-7 and FDC-P1 cell proliferation was assessed by AlamarBlue (BioSource International Inc., Camarillo, Calif. 93012, USA). Briefly, the cells were plated into 96-well Costar cell culture plate (Corning Incorporated, Corning, N.Y. 14831, USA) at 7000 cells/well and 4000 cells/well for UT7/EPO and FDC-P1 cell line, respectively. The test compound and/or vehicle was added to each well with a final concentration of 1% DMSO and incubated in an atmosphere of 5% $CO_2$ at 37° C. for 66 hours. After a further 6 hour incubation in the presence of AlamarBlue, fluorescent intensity was measured using a SpectraMax Gemini (Molecular Devices, Sunnyvale, Calif. 94089, USA) plate reader, with excitation at 530 nm and emission at 590 nm. The Percent Increase=((RFU Test-RFU Medium)/(RFU Vehicle-RFU Medium)-1)*100. Recombinant human EPO (Research Diagnostics, Inc., Flanders, N.J. 07836, USA) was used in the assay as a positive control.

Examples in Table 1 were assayed according to the method described for the UT-7 assay above, and all except Example 4 showed about 20% or more cell proliferation in the UT-7 assay at or below 1000 micromolar compound concentration.

While the invention has been described and illustrated with reference to certain embodiments therof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the mammal being treated for erythropoietin-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. The compound of Formula (I):

wherein
  c is equal to 0;
  G is: —$CO_2R_1$;
  wherein
    $R_1$ is -hydrogen;
  V is: —$CH_2$—;
  X is —$N(R_8)CO$—,
  wherein
    $R_8$ is: -hydrogen;
  $Ar_1$ is a mono-substituted phenyl group, wherein the substituent is selected from the group consisting of: -aryl, -arylene-alkyl, -D-aryl, -D-alkylene-arylene-alkyl, -arylene-D-alkyl, -arylene-D-$R_{10}$, and -D-alkylene-arylene-aryl,
  wherein
    $R_{10}$ is -aryl or -alkylene-aryl, and
    D is —O—, or —$N(R_{11})$—,
      wherein $R_{11}$ is: -hydrogen, -alkyl, or -aryl;
  $Ar_2$ is a substituted phenyl having 2 to 5 substituents wherein the phenyl is substituted at an ortho and a meta position on $Ar_2$, relative to X; and wherein the substituents are independently selected from the group consisting of: -fluoro, -chloro, -bromo, iodo, -cyano, -nitro, - perfluoroalkyl, -$T_1$-$R_{14}$, -alkyl, -aryl, -arylene-alkyl, -$T_1$-alkyl, -$T_1$-alkylenearyl, -T$_1$-alkylene-arylene-aryl, -T$_1$-alkylene-arylene-alkyl, -arylene-T$_1$-alkyl, -T$_1$-arylene-aryl, -T$_1$-arylene-alkyl, -T$_1$-aryl, -T$_1$-alkylene-T$_2$-R$_{14}$ and -T$_1$-arylene-T$_2$-R$_{14}$;

wherein

T$_1$ and T$_2$ are independently selected from the group consisting of —CH$_2$—, —O—, —N(R$_{15}$)—, —CON(R$_{15}$)—, —N(R$_{15}$)C(O), —N(R$_{15}$)SO$_2$, and —C(O)—O—;

wherein

R$_{14}$ and R$_{15}$ are independently selected from the group consisting of: -hydrogen, -alkyl, and -aryl, and wherein the alkyl, aryl alkylene, and arylene groups in Ar$_1$, Ar$_2$, and R$_{10}$, R$_{11}$, R$_{14}$, and R$_{15}$, may be optionally substituted 1 to 4 times with a substituent, wherein the substituents are independently selected from the group consisting of:

a) -hydrogen;
b) -fluoro;
c) -chloro;
d) -bromo;
e) -iodo;
f) -cyano;
g) -nitro;
h) -perfluoroalkyl;
i) -Q-R$_{18}$;
j) -Q-alkyl;
k) -Q-aryl;
l) -Q-alkylene-aryl;
m) -Q-alkylene-NR$_{19}$R$_{20}$; and
n) -Q-alkyl-W—R$_{21}$;

wherein

Q and W are independently selected from the group consisting of: —CH$_2$—, —O—, —N(R$_{22}$)—, —C(O)—, —CON(R$_{22}$)—, —N(R$_{22}$)C(O)—, —N(R$_{22}$)CON(R$_{23}$)—, —N(R$_{22}$)C(O)O—, —OC(O)N(R$_{22}$)—, —N(R$_{22}$)SO$_2$—, —SO$_2$N(R$_{22}$)—, —C(O)—O—, —O—C(O)—, and —N(R$_{22}$)SO$_2$N(R$_{23}$)—, wherein R$_{18}$, R$_{19}$, R$_{20}$, R$_{21}$, R$_{22}$, and R$_{23}$ are independently selected from the group consisting of: -hydrogen, -alkyl, -aryl, -arylene-alkyl, -alkylene-aryl, and -alkylene-arylene-alkyl, or a pharmaceutically acceptable salt thereof.

2. The compound of Formula (I) in claim 1, wherein

Ar$_1$ is: biphenyl-4-yl;
trifluoromethyl-biphenyl-4-yl;
(biphenyl-4-ylmethoxy)-phenyl;
(tert-butyl-benzyloxy)-phenyl; or
4'-phenoxy-biphenyl-4-yl, or a pharmaceutically acceptable salt thereof.

3. The compound of Formula (I) in claim 1, wherein

Ar$_2$ and X together form a group selected from:
[bromo-(tert-butyl-benzenesulfonylamino)]-benzoylamino;
(3'-chloro-4'-fluoro-4-hydroxy-biphenyl-3-carbonyl)-amino;
{chloro-[(naphthalen-1-yl-methyl)-amino]}-benzoylamino;
[(bistrifluoromethyl-benzoylamino)-bromo]-benzoylamino;
[chloro-(carboxyhexylamino)]-benzoylamino;
{chloro-[(dimethylamino-naphthalene)-sulfonylamino]}-benzoylamino;
[chloro-(2-methyl-pentylamino)]-benzoylamino;
[(biphenyl-sulfonylamino)-chloro]-benzoylamino;
[chloro-(2-methyl-butylamino)]-benzoylamino;
{chloro-[N-(carboxyhexyl)-N'-(bis-trifluoromethyl-benzoyl)-amino)]}-benzoylamino; and
{[N-(bis-trifluoromethyl-benzoyl)-N'-pentylamino]-chloro}-benzoylamino, or a pharmaceutically acceptable salt thereof.

4. A compound of Formula (I) as in claim 1 selected from the group consisting of:

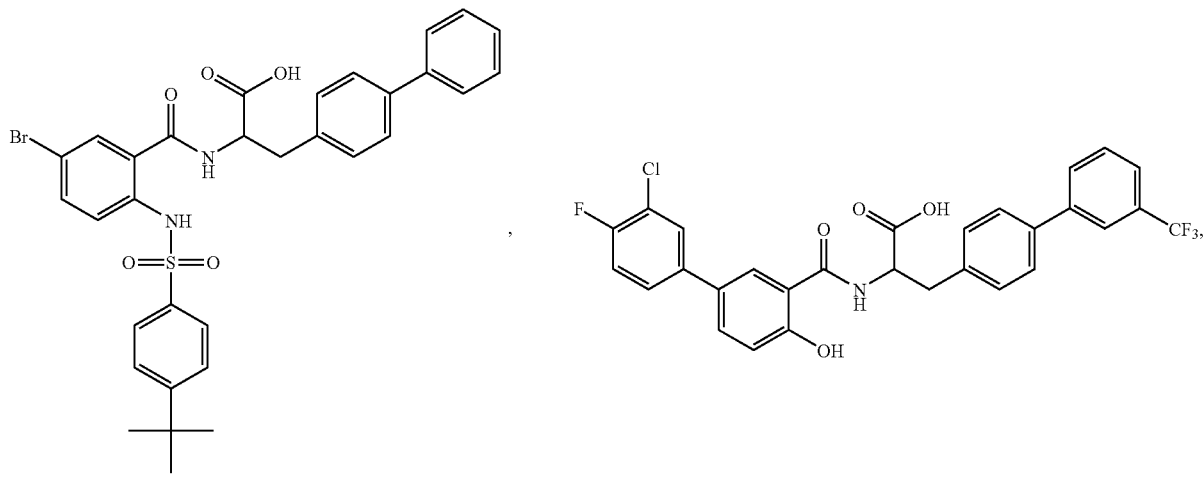

-continued
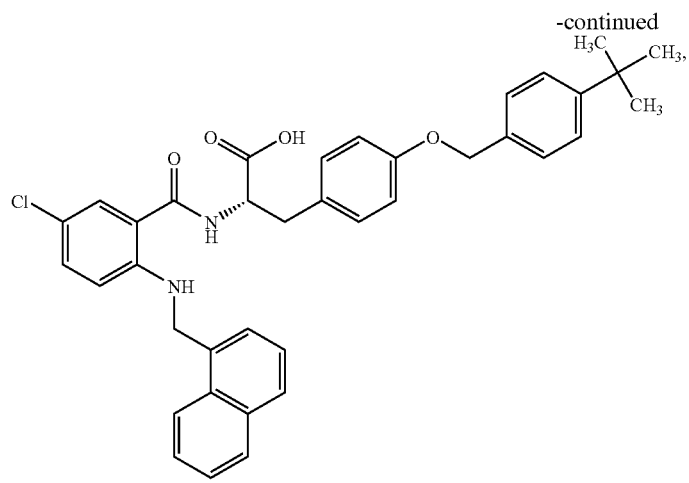
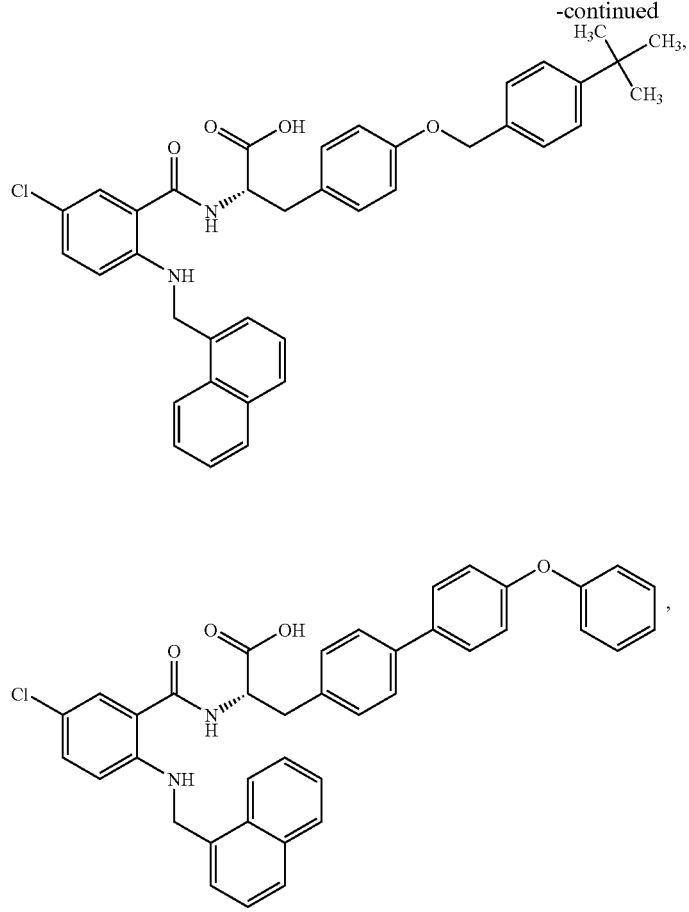
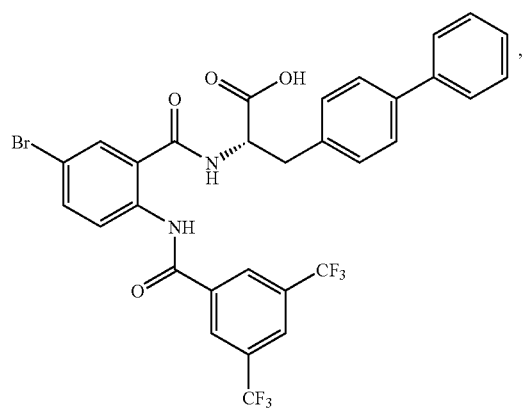
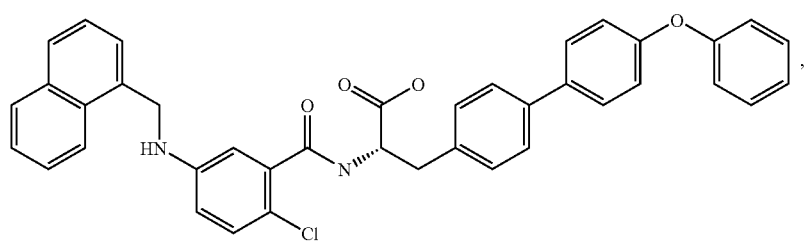

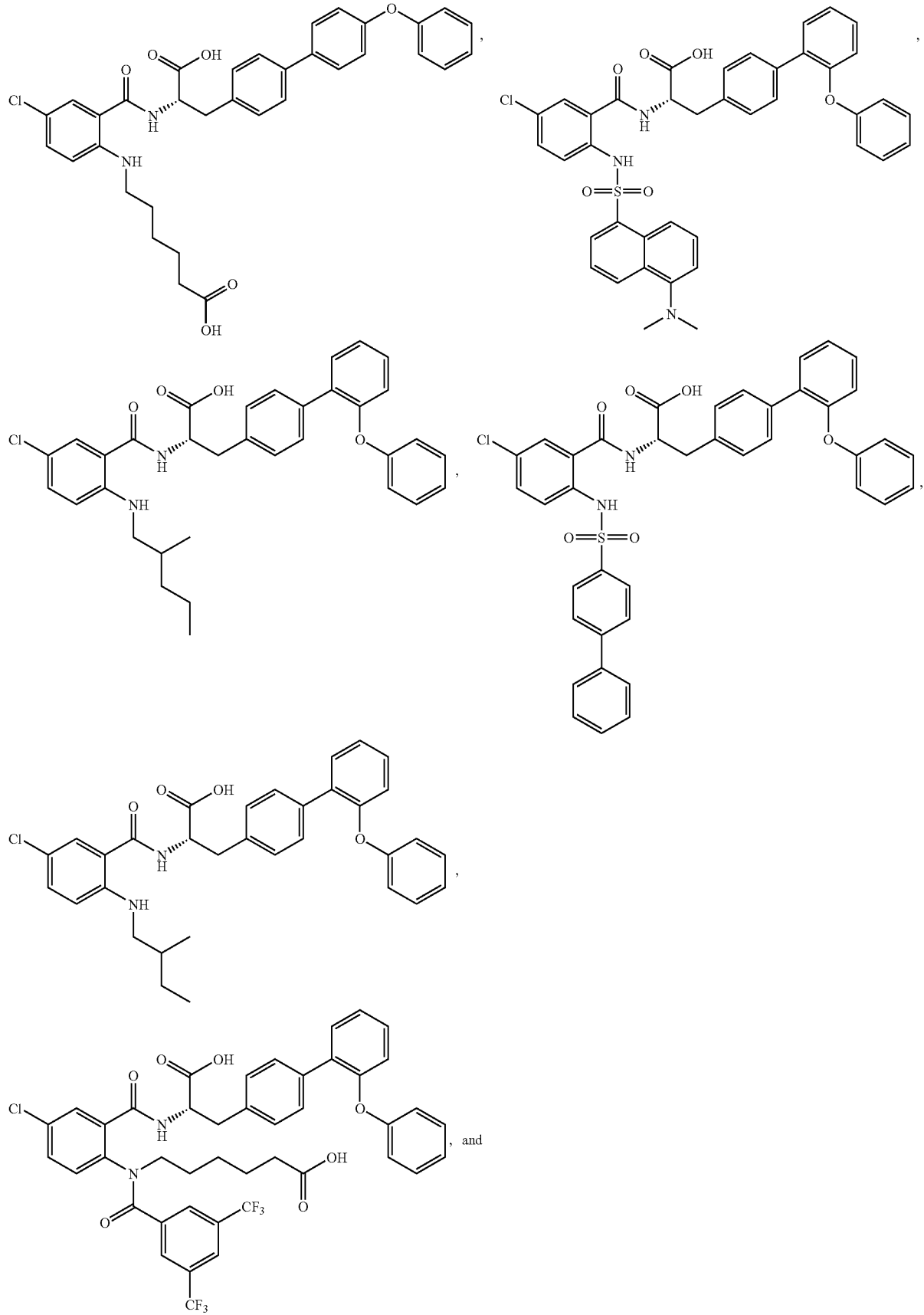

-continued or a pharmaceutically acceptable salt thereof.

5. A pharmaceutical composition comprising a compound of Formula (I) wherein $$\text{(I)}$$

c is equal to 0;
G is: —CO$_2$R$_1$;
wherein
R$_1$ is -hydrogen;
V is: —CH$_2$—;
X is —N(R$_8$)CO—,
wherein
R$_8$ is: -hydrogen;
Ar$_1$ is a mono-substituted phenyl group, wherein the substituent is selected from the group consisting of: -aryl, -arylene-alkyl, -D-aryl, -D-alkylene-arylene-alkyl, -arylene-D-alkyl, -arylene-D-R$_{10}$, and -D-alkylene-arylene-aryl,
wherein
R$_{10}$ is -aryl or -alkylene-aryl, and
D is —O—, or —N(R$_{11}$)—,
wherein R$_{11}$ is: -hydrogen, -alkyl, or -aryl;
Ar$_2$ is a substituted phenyl having 2 to 5 substituents wherein the phenyl is substituted at an ortho and a meta position on Ar$_2$ relative to X; and wherein the substituents are independently selected from the group consisting of: -fluoro, -chloro, -bromo, iodo, -cyano, -nitro, -perfluoroalkyl, -T$_1$-R$_{14}$, -alkyl, -aryl, -arylene-alkyl, -T$_1$-alkyl, -T$_1$-alkylene-aryl, -T$_1$-alkylene-arylene-aryl, -T$_1$-alkylene-arylene-alkyl, -arylene-T$_1$-alkyl, -T$_1$-arylene-aryl, -T$_1$-arylene-alkyl, -T$_1$aryl, -T$_1$alkylene-T$_2$-R$_{14}$, and -T$_1$-arylene-T$_2$-R$_{14}$;
wherein
T$_1$ and T$_2$ are independently selected from the group consisting of —CH$_2$—, —O—, —N(R$_{15}$—, —CON(R$_{15}$)—, —N(R$_{15}$)C(O), —N(R$_{15}$)SO$_2$, and —C(O)—O—;
wherein
R$_{14}$ and R$_{15}$ are independently selected from the group consisting of: -hydrogen, -alkyl, and -aryl,
and wherein
the alkyl, aryl, alkylene, and arylene groups in Ar$_1$, Ar$_2$, and R$_{10}$, R$_{11}$, R$_{14}$, and R$_{15}$, may be optionally substituted 1 to 4 times with a substituent, wherein the substituents are independently selected from the group consisting of:

a) -hydrogen;
b) -fluoro
c) -chloro;
d) -bromo
e) -iodo;
f) -cyano;
g) -nitro;
h) -perfluoroalkyl;
i) -Q-R$_{18}$;
j) -Q-alkyl;
k) -Q-aryl;
l) -Q-alkylene-aryl;
m) -Q-alkylene-NR$_{19}$R$_{20}$; and
n) -Q-alkyl-W—R$_{21}$;
wherein
Q and W are independently selected from the group consisting of: —CH$_2$—, —O—, —N(R$_{22}$)—, —C(O)—, —CON(R$_{22}$)—, —N(R$_{22}$)C(O)—, —N(R$_{22}$)CON(R$_{23}$)—, —N(R$_{22}$)C(O)O—, —OC(O)N(R$_{22}$)—, —N(R$_{22}$)SO$_2$—, —SO$_2$N(R$_{22}$)—, —C(O)—O—, —O—C(O)—, and —N(R$_{22}$)SO$_2$N(R$_{23}$)—, wherein
R$_{18}$, R$_{19}$, R$_{20}$, R$_{21}$, R$_{22}$, and R$_{23}$, are independently selected from the group consisting of: -hydrogen, -alkyl, -aryl, -arylene-alkyl, -alkylene-aryl, and -alkylene-arylene-alkyl,
or a pharmaceutically acceptable salt thereof.

6. The pharmaceutical composition of claim 5, further comprising one or more pharmaceutically acceptable carriers, excipients, or diluents.

7. The pharmaceutical composition of claim 5, comprising a therapeutically effective amount of the compound.

8. The pharmaceutical composition of claim 7, wherein a therapeutically effective amount of the compound is an amount sufficient to treat a disease mediated at least in part by an erythropoietin receptor.

9. The pharmaceutical composition of claim 5, wherein the compound binds to an erythropoietin receptor.

10. The pharmaceutical composition of claim 5, wherein the compound activates erythropoietin receptor-mediated signal transduction.

11. The pharmaceutical composition of claim 5, wherein the compound induces red blood cell production mediated by erythropoietin receptor activation.

12. The pharmaceutical composition of claim 5, in the form of an oral dosage unit.

13. The pharmaceutical composition of claim 5, in the form of or parenteral dosage unit.

14. The pharmaceutical composition of claim 5, wherein said compound is a dose in a range from about 0.01 to 1,000 mg/kg of body weight per day.

15. The pharmaceutical composition of claim 5, wherein said compound is a dose in a range from about 0.1 to 100 mg/kg of body weight per day.

16. The pharmaceutical composition of claim 5, wherein said compound is a dose in a range from about 0.5 to 10 mg/kg of body weight per day.

17. The pharmaceutical composition of claim 8, wherein the disease mediated by an erythropoietin receptor comprises anemia of renal failure.

18. The pharmaceutical composition of claim 8, wherein the disease mediated by an erythropoietin receptor comprises anemia of end-stage renal disease.

19. The pharmaceutical composition of claim 8, wherein the disease mediated by an erythropoietin receptor comprises anemia of chronic disorders.

20. The pharmaceutical composition of claim 8, wherein the disease mediated by an erythropoietin receptor comprises anemia of chronic infection.

21. The pharmaceutical composition of claim 8, wherein the disease mediated by an erythropoietin receptor comprises anemia of rheumatoid arthritis.

22. The pharmaceutical composition of claim 8, wherein the disease mediated by an erythropoietin receptor comprises anemia of autoimmune disease.

23. The pharmaceutical composition of claim 8, wherein the disease mediated by an erythropoietin receptor comprises anemia of AIDS.

24. The pharmaceutical composition of claim 8, wherein the disease mediated by an erythropoietin receptor comprises anemia of malignancy.

25. The pharmaceutical composition of claim 5, further comprising one or more additional therapeutic agents.

26. The pharmaceutical composition of claim 5, wherein $Ar_1$ is: biphenyl-4-yl;
trifluoromethyl-biphenyl-4-yl;
(biphenyl-4-ylmethoxy)-phenyl;
(tert-butyl-benzyloxy)-phenyl; or
4'-phenoxy-biphenyl-4-yl.

27. The pharmaceutical composition of claim 5, wherein $Ar_2$ and X together form a group selected from:
[bromo-(tert-butyl-benzenesulfonylamino)]-benzoylamino;
(3'-chloro-4'-fluoro-4-hydroxy-biphenyl-3-carbonyl)-amino;
{chloro-[(naphthalen-1-yl-methyl)-amino]}-benzoylamino;
[(bistrifluoromethyl-benzoylamino)-bromo]-benzoylamino;
[chloro-(carboxyhexylamino)]-benzoylamino;
{chloro-[(dimethylamino-naphthalene)-sulfonylamino]}-benzoylamino;
[chloro-(2-methyl-pentylamino)]-benzoylamino;
[(biphenyl-sulfonylamino)-chloro]-benzoylamino;
[chloro-(2-methyl-butylamino)]-benzoylamino;
{chloro-[N-(carboxyhexyl)-N'-(bis-trifluoromethyl-benzoyl)-amino)]}-benzoylamino; and
{[N-(bis-trifluoromethyl-benzoyl)-N'-pentylamino]-chloro}-benzoylamino.

28. The pharmaceutical composition of claim 5, wherein the compound of Formula (I) is selected from the group consisting of:

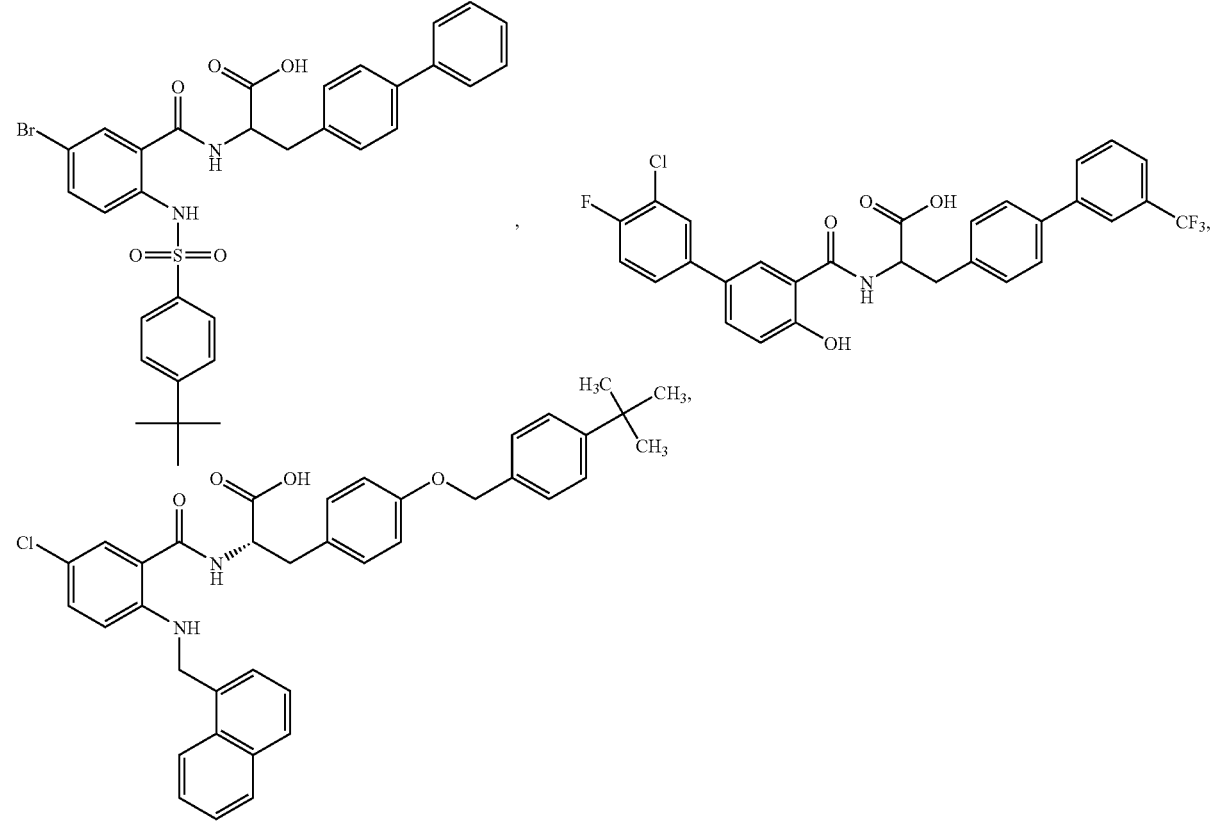

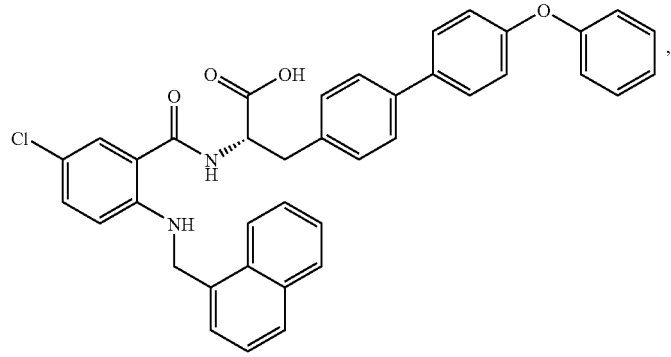
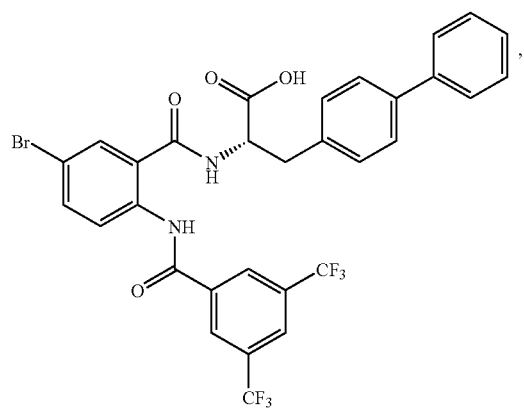
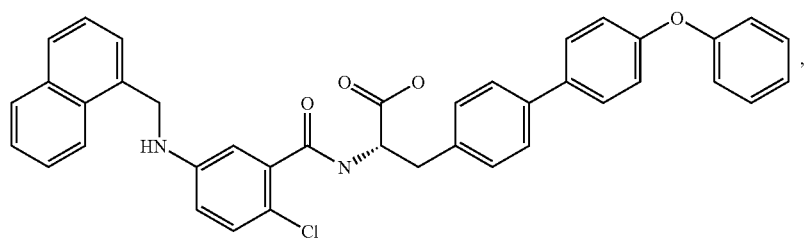
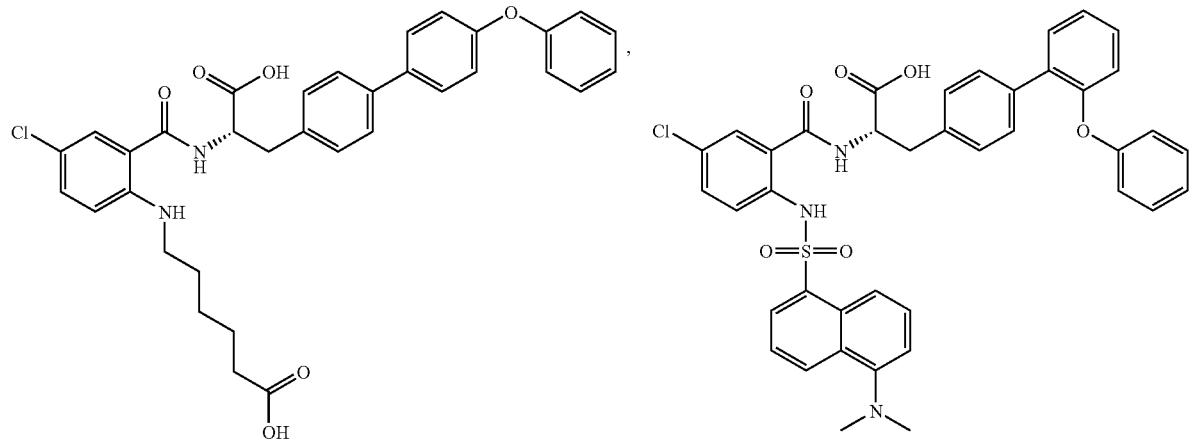

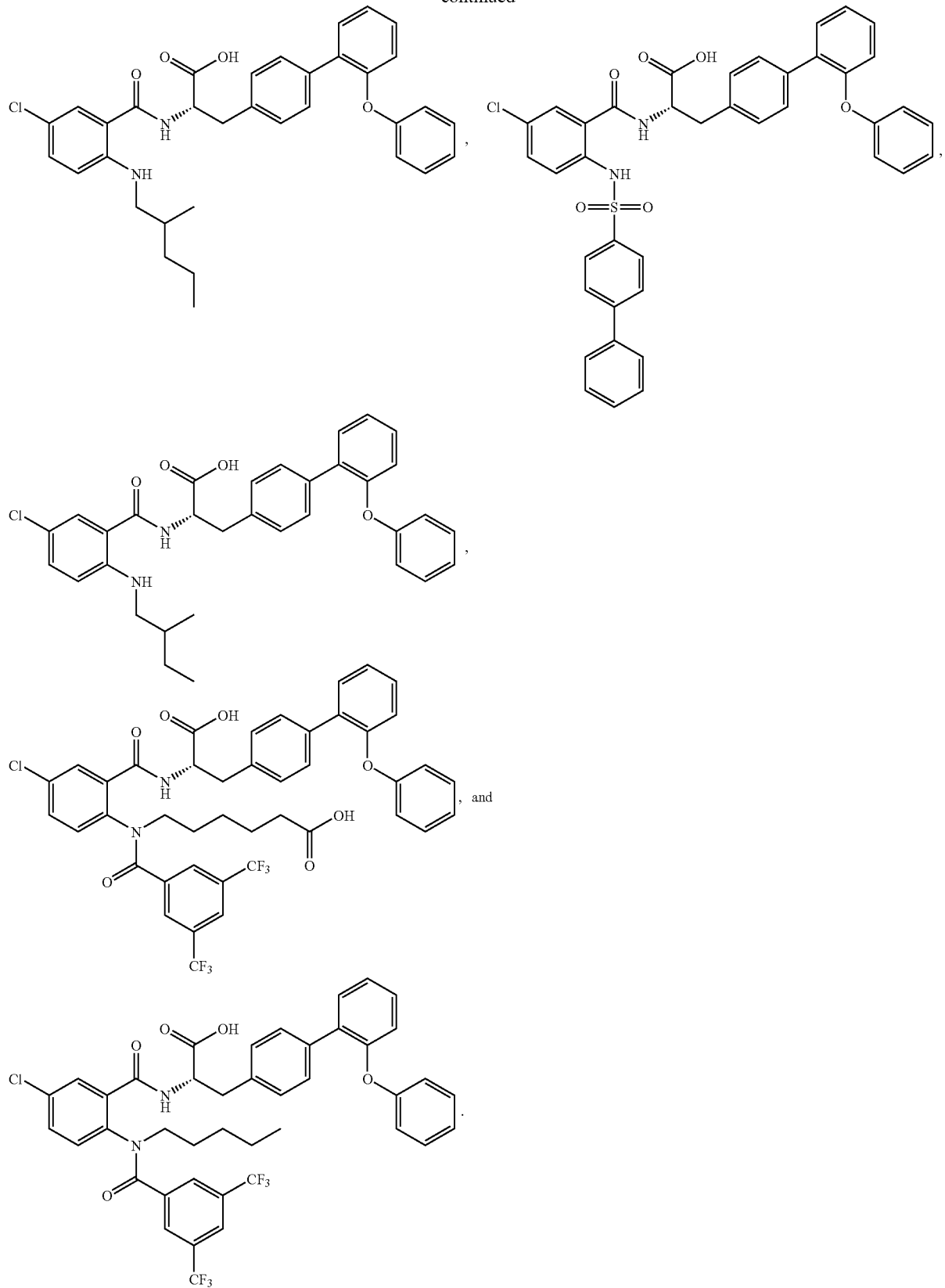
or a pharmaceutically acceptable salt thereof.
* * * * *

UNITED STATES PATENT AND TRADEMARK OFFICE
CERTIFICATE OF CORRECTION

PATENT NO.      : 7,501,538 B2                          Page 1 of 5
APPLICATION NO. : 10/913882
DATED           : March 10, 2009
INVENTOR(S)     : Adnan M. M. Mjalli et al.

It is certified that error appears in the above-identified patent and that said Letters Patent is hereby corrected as shown below:

Column 1, line 9, please delete "Antviral", please insert -- Antiviral --.

Column 1, lines 57-58 (Approx.), please delete "erythoid", please insert -- erythroid --.

Column 3, line 54 (Approx.), please delete "hemoblobin", please insert -- hemoglobin --.

Column 5, line 15, please delete "$R_g$", please insert -- $R_9$ --.

Column 6, line 26, please delete "compromises", please insert -- comprises --.

Column 6, line 32, please delete "4'-phenoxy-biphenyl4-yl.", please insert
-- 4'-phenoxy-biphenyl-4-yl. --.

Column 6, line 51, please delete "i)", please insert -- j) --.

Column 7, line 2, after "$R_{14}$" please insert -- ; --.

Column 7, line 19 (Approx.), please delete "O-C(O)-,", please insert -- -O-C(O)-, --.

Column 7, line 53 (Approx.), after "$R_{14}$" please insert -- ; --.

Column 8, line 9, please delete "( bis", please insert -- (bis --.

Columns 11-12 (Table 1), lines 5-6, please delete "propioinic", please insert -- propionic --.

Columns 11-12 (Table 1), line 16, please delete "propioinic", please insert -- propionic --.

Column 20, line 60 (Approx.), please delete "dily," please insert -- diyl, --.

Column 21, line 25, after "like" please insert -- . --.

Signed and Sealed this

Twenty-fifth Day of May, 2010

David J. Kappos
*Director of the United States Patent and Trademark Office*

Column 22, line 36 (Approx.), please delete "-$CH_2$-NH-$H_3$", please insert -- -$CH_2$-NH-$CH_3$ --.

Column 22, line 40, please delete "sunstantially", please insert -- substantially --.

Column 24, line 66, please delete "compouind", please insert -- compound --.

Column 25, line 2, please delete "II,", please insert -- III, --.

Column 25, line 62 (Approx.), please delete "plladium(0),", please insert -- palladium(0), --.

Column 26, line 37, please delete "iodo-subsituted", please insert -- iodo-substituted --.

Column 27, line 23 (Approx.), please delete "Merrifiend", please insert -- Merrifield --.

Column 28, line 8, please delete "plladium(0),", please insert -- palladium(0), --.

Column 28, line 18, please delete "plladium(0),", please insert -- palladium(0), --.

Column 29, line 55, please delete "iodo-subsituted", please insert -- iodo-substituted --.

Column 30 (Scheme IX), line 10, please delete " 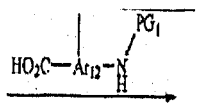 ", please insert -- 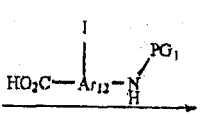 --.

Column 31, line 37 (Approx.), please delete "phenyldimethylsilyi,", please insert -- phenyldimethylsilyl, --.

Column 31, line 38 (Approx.), please delete "triiospropylsilyl", please insert -- triisopropylsilyl --.

Column 31, line 56 (Approx.), please delete "triiospropylsilyl", please insert -- triisopropylsilyl --.

Column 33, line 22, please delete "alchol,", please insert -- alcohol, --.

Column 34, lines 29-30, please delete "Glycollylarsanilate", please insert -- Glycolylarsanilate --.

Column 34, line 31, please delete "Hydrocloride,", please insert -- Hydrochloride, --.

Column 34, line 33, please delete "Methyinitrate,", please insert -- MethyInitrate, --.

Column 34, line 46, please delete "oxlate", please insert -- oxalate --.

Column 34, line 62, please delete "therof,", please insert -- thereof, --.

Column 35, line 6 (Approx.), please delete "therof,", please insert -- thereof, --.

CERTIFICATE OF CORRECTION (continued)
U.S. Pat. No. 7,501,538 B2

Column 35, line 67, please delete "Mefformin", please insert -- Metformin --.

Column 36, line 44, please delete "saquanivir", please insert -- saquinivir --.

Column 36, line 46, After "valaciclovir" please insert -- . --.

Column 39, line 65, please delete "re-esterfied", please insert -- re-esterified --.

Column 40, line 58, please delete "magesium", please insert -- magnesium --.

Column 42, line 3, please delete "fluoro4", please insert -- fluoro-4 --.

Column 42, line 4, please delete "biphenyl4", please insert -- biphenyl-4 --.

Column 42, line 46, please delete "biphenyl4", please insert -- biphenyl-4 --.

Column 43, line 1, please delete "biphenyl4", please insert -- biphenyl-4 --.

Column 43, lines 57-58, please delete "propioinic", please insert -- propionic --.

Column 44, lines 2-3, please delete "propioinic", please insert -- propionic --.

Column 45, line 22, please delete "benzoylamino]propionic", please insert
-- benzoylamino] propionic --.

Column 45, line 25 (Approx.), please delete "compound.The", please insert -- compound. The --.

Column 45, line 32-33, please delete "propioinic", please insert -- propionic --.

Column 46, line 2, please delete "propioinic", please insert -- propionic --.

Column 46, line 5 (Approx.), please delete "propioinic", please insert -- propionic --.

Column 46, line 45, please delete "NaBH(OAc)$_3$was", please insert -- NaBH(OAc)$_3$ was --.

Column 47, line 45, please delete "mmol,).", please insert -- mmol). --.

Column 48, line 7, please delete "biphenyl4", please insert -- biphenyl-4 --.

Column 48, line 21, please delete "biphenyl4", please insert -- biphenyl-4 --.

Column 48, line 50, please delete "propionicacid", please insert -- propionic acid --.

Column 50, line 32 (Approx.), After "(M+1)+", please insert -- . --.

Column 52, line 12 (Approx.), please delete "therof,", please insert -- thereof, --.

Column 52, line 56, In Claim 1, please delete "-arylene-D-R$_{10,}$", please insert -- -arylene-D-R$_{10}$, --.

Column 52, line 64, In Claim 1, please delete "Ar$_2$,", please insert -- Ar$_2$ --.

Column 52, line 66, In Claim 1, please delete "iodo,", please insert -- -iodo, --.

Column 53, line 3, In Claim 1, please delete "-T$_1$-alkylene-T$_2$-R$_{14}$", please insert -- -T$_1$alkylene-T$_2$-R$_{14}$, --.

Column 53, line 13 (Approx.), In Claim 1, please delete "aryl", please insert -- aryl, --.

Column 53, line 22, In Claim 1, please delete "-bromo", please insert -- bromo; --.

Column 53, line 31, In Claim 1, please delete "I)", please insert -- l) --.

Column 59, line 1, In Claim 4, please delete " 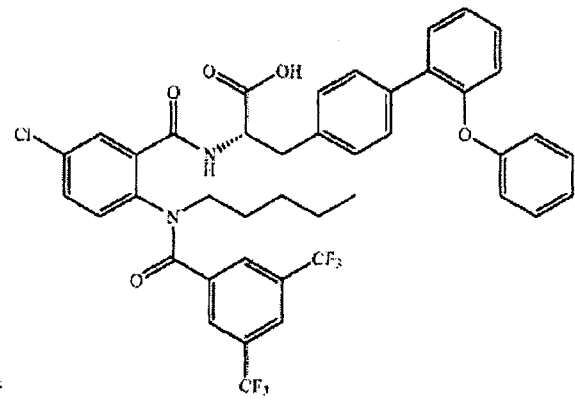 ", please insert -- 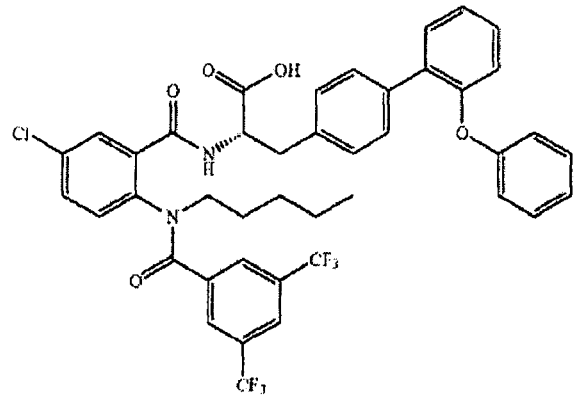 , --.

CERTIFICATE OF CORRECTION (continued)
U.S. Pat. No. 7,501,538 B2

Column 59, line 41, In Claim 5, please delete "-arylene-D-R$_{10,}$,", please insert -- -arylene-D-R$_{10}$, --.

Column 59, line 50, In Claim 5, please delete "iodo,", please insert -- -iodo, --.

Column 59, line 54, In Claim 5, please delete "-T$_1$aryl, -T$_1$alkylene-T$_2$-R$_{14}$,", please insert -- -T$_1$-aryl, -T$_1$-alkylene-T$_2$-R$_{14}$, --.

Column 59, line 57, In Claim 5, please delete "-N(R$_{15}$-,", please insert -- -N(R$_{15}$)-, --.

Column 60, line 22, In Claim 5, please delete "-fluoro", please insert -- -fluoro; --.

Column 60, line 24, In Claim 5, please delete "-bromo", please insert -- -bromo; --.

Column 60, line 33, In Claim 5, please delete "I)", please insert -- l) --.

Column 61, lines 3-4, In Claim 13, please delete "or", please insert -- a --.

Column 65, line 4, In Claim 28, please delete " 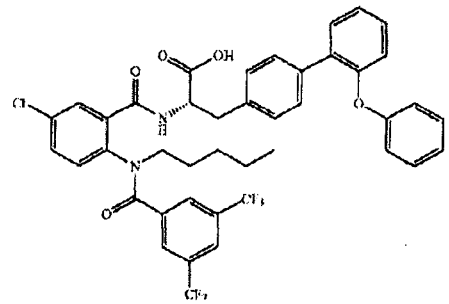 ", please insert -- 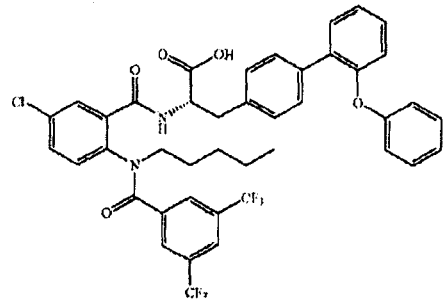 , --.